United States Patent
Malik et al.

(10) Patent No.: US 8,685,240 B2
(45) Date of Patent: Apr. 1, 2014

(54) HIGH EFFICIENCY SOL-GEL GAS CHROMATOGRAPHY COLUMN

(75) Inventors: Abdul Malik, Tampa, FL (US); Abuzar Kabir, Tampa, FL (US); Chetan Shende, Vernon, CT (US)

(73) Assignee: University of South Florida, Tampa, FL (US)

( * ) Notice: Subject to any disclaimer, the term of this patent is extended or adjusted under 35 U.S.C. 154(b) by 1875 days.

(21) Appl. No.: 11/599,497

(22) Filed: Nov. 13, 2006

(65) Prior Publication Data

US 2007/0062874 A1   Mar. 22, 2007

Related U.S. Application Data

(63) Continuation of application No. 10/471,388, filed as application No. PCT/US02/07163 on Mar. 8, 2002, now abandoned.

(60) Provisional application No. 60/274,886, filed on Mar. 9, 2001.

(51) Int. Cl.
*B01J 20/285* (2006.01)
*B01J 20/28* (2006.01)
*B01D 15/26* (2006.01)
*G01N 30/56* (2006.01)
*G01N 30/60* (2006.01)

(52) U.S. Cl.
CPC .......... *B01J 20/285* (2013.01); *B01J 20/28047* (2013.01); *B01D 15/265* (2013.01); *G01N 30/56* (2013.01); *G01N 30/6078* (2013.01)
USPC .................... 210/198.2; 210/502.1; 210/635; 210/656; 96/101

(58) Field of Classification Search
CPC ... B01D 15/206; B01D 15/265; B01J 20/265; B01J 20/285; B01J 20/286; B01J 20/28047; G01N 30/56; G01N 30/6078
USPC ................. 210/198.2, 635, 656, 659, 502.1; 422/70; 436/161, 178; 96/101
See application file for complete search history.

(56) References Cited

U.S. PATENT DOCUMENTS

3,722,181 A   3/1973   Kirkland et al.
3,954,651 A   5/1976   Donike (Continued)

FOREIGN PATENT DOCUMENTS

EP   0315633 B1   10/1991
EP   0537851 B1   3/1996

(Continued)

OTHER PUBLICATIONS

Aichholz, R., "Preparation of Glass Capillary Columns Coated with OH-Terminated (3,3,3-Trifluoropropyl) Methyl Polysiloxane (PS 184.5)", *Journal of High Resolution Chromatography*, 13, 71-73 (1990).

(Continued)

*Primary Examiner* — Ernest G Therkorn
(74) *Attorney, Agent, or Firm* — Saliwanchik, Lloyd & Eisenschenk

(57) ABSTRACT

A capillary column (10) includes a tube structure having inner walls (14) and a sol-gel substrate (16) coated on a portion of inner walls (14) to form a stationary phase coating (18) on inner walls (14). The sol solution used to prepare the sol-gel substrate (16) has at least one baseline stabilizing reagent and at least one surface deactivation reagent resulting in the sol-gel substrate (16) having at least one baseline stabilizing reagent residual and at least one surface deactivating reagent residual. A method of making the sol-gel solution is by mixing suitable sol-gel precursors to form the solution, stabilizing the solution by adding at least one baseline stabilization reagent, deactivating the solution by adding at least one surface deactivation reagent to the solution, and reacting the solution in the presence of at least one catalyst.

9 Claims, 17 Drawing Sheets

(56) References Cited

U.S. PATENT DOCUMENTS

| | | | |
|---|---|---|---|
| 4,199,330 | A | 4/1980 | Nestrick et al. |
| 4,276,061 | A | 6/1981 | Nestrick et al. |
| 4,509,964 | A | 4/1985 | Hubball et al. |
| 4,966,785 | A | 10/1990 | Springston |
| 5,128,291 | A | 7/1992 | Wax et al. |
| 5,145,579 | A | 9/1992 | Eguchi et al. |
| 5,154,822 | A | 10/1992 | Simpson et al. |
| 5,192,406 | A | 3/1993 | Woolley |
| 5,262,052 | A | 11/1993 | Rossiter et al. |
| 5,268,442 | A | 12/1993 | Bradshaw et al. |
| 5,270,027 | A | 12/1993 | Balducci et al. |
| 5,292,801 | A | 3/1994 | Avnir et al. |
| 5,300,564 | A | 4/1994 | Avnir et al. |
| 5,308,495 | A | 5/1994 | Avnir et al. |
| 5,322,608 | A | 6/1994 | Karger et al. |
| 5,360,878 | A | 11/1994 | Shen |
| 5,371,018 | A | 12/1994 | Avnir et al. |
| 5,403,898 | A | 4/1995 | Bradshaw et al. |
| 5,589,396 | A | 12/1996 | Frye et al. |
| 5,624,875 | A | 4/1997 | Nakanishi et al. |
| 5,637,135 | A | 6/1997 | Ottenstein et al. |
| 5,650,311 | A | 7/1997 | Avnir et al. |
| 5,653,875 | A | 8/1997 | Betz et al. |
| 5,679,576 | A | 10/1997 | Kawai et al. |
| 5,691,206 | A | 11/1997 | Pawliszyn et al. |
| 5,750,197 | A * | 5/1998 | van Ooij et al. ............ 427/308 |
| 5,824,526 | A | 10/1998 | Avnir et al. |
| 5,840,388 | A | 11/1998 | Karger et al. |
| 5,869,152 | A | 2/1999 | Colon |
| 5,900,145 | A | 5/1999 | Naikwadi et al. |
| 6,136,187 | A | 10/2000 | Zare et al. |
| 6,344,242 | B1 | 2/2002 | Stolk et al. |
| 6,423,770 | B1 * | 7/2002 | Katz ............................ 524/492 |
| 6,613,234 | B2 | 9/2003 | Voute et al. |
| 6,759,126 | B1 | 7/2004 | Malik et al. |
| 6,783,680 | B2 | 8/2004 | Malik |
| 6,998,040 | B2 | 2/2006 | Malik et al. |
| 2003/0075447 | A1 | 4/2003 | Malik et al. |
| 2003/0213732 | A1 | 11/2003 | Malik et al. |
| 2004/0129141 | A1 | 7/2004 | Malik et al. |
| 2005/0106068 | A1 | 5/2005 | Malik et al. |
| 2006/0013981 | A1 | 1/2006 | Malik et al. |
| 2006/0013982 | A1 | 1/2006 | Malik et al. |
| 2006/0113231 | A1 | 6/2006 | Malik et al. |
| 2007/0062874 | A1 | 3/2007 | Malik et al. |
| 2007/0095736 | A1 | 5/2007 | Malik et al. |
| 2007/0172960 | A1 | 7/2007 | Malik et al. |

FOREIGN PATENT DOCUMENTS

| | | |
|---|---|---|
| EP | 0439318 B1 | 5/1998 |
| JP | 04 370760 | 12/1992 |
| WO | WO 88/00860 | 2/1988 |
| WO | WO 99/30147 | 6/1999 |
| WO | WO 00/11463 | 3/2000 |
| WO | WO 02/072225 | 9/2002 |
| WO | WO 02/094410 | 11/2002 |

OTHER PUBLICATIONS

Alltech, *Chromatography Catalog*, 172 (1997).

Altgelt, K. et al., *Chromatography in Petroleum Analysis*, Marcel Dekker, Inc., New York and Basel (1979).

Albin, M. et al. "Sensitivity Enhancement for Capillary Electrophoresis", *Analytical Chemistry*, 65, 489-497A (1993).

Alhooshani, K. et al. "Sol-Gel Approach to in situ Creation of High pH-resistant surface-bonded Organic-Inorganic Hybrid Zirconia Coating for Capillary Microextraction (in-tube SPME)" *Journal of Chromatography A*, 1065, 1-14 (2005).

Belardi, R. et al., "The Application of Chemically Modified Fused Silica Fibers in the Extraction of Organics from Water Matrix Samples and their Rapid Transfer to Capillary Columns", *Water Pollut. Res. J. Can.*, 24, 179-191 (1989).

Berezkin, V.G. et al., "Capillary Columns with Several Layers of Different Immobilized Stationary Phases", *J. Anal. Chem.—USSR*, 47, 600-604 (1992).

Berezkin, V.G. et al., *Gas Chromatography in Air Pollution Analysis*, Elsevier, Amsterdam—Oxford—New York—Tokyo, Chapter 8, 165-207 (1991).

Bigham, S. et al. "Sol-Gel Capillary Microextraction", *Anal. Chem.* 74, 752-761 (2002).

Blau, K. et al., eds., *Handbook of Derivatives for Chromatography*, $2^{nd}$ ed., John Wiley & Sons, Chichester—New York—Brisbane—Toronto—Singapore, 1-30 (1993).

Blomberg, L. et al., "Modification of Glass Capillary Columns by Cyclic (3,3,3-Trifluoropropyl)methylsiloxanes", *Journal of HRC & CC*, 3, 527-528 (1980).

Brinker, C.J. et al., *Sol-Gel Science: The Physics and Chemistry of Sol-Gel Processing*, Academic Press, San Diego—New York—Boston—London—Sydney—Tokyo—Toronto, 97-233 (1990).

Britz-McKibbin, P. et al. "Selective Focusing of Catecholamines and Weakly Acidic Compounds by Capillary Electrophoresis Using a Dynamic pH Junction", *Anal. Chem.*, 72, 1242-1252 (2000).

Britz-McKibbin, P. et al. "On-Line Focusing of Flavin Derivative Using Dynamic pH Junction-Sweeping Capillary Electrophoresis with Laser-Induced Fluorescence Detection", *Anal. Chem.*, 74, 3736-3743 (2002).

Brown, P. B. et al. "The Separation and the Characterization of Long Chain Fatty Acids and Their Derivatives by Reversed Phase High Performance Liquid Chromatography", *Analytical Chemistry*, 21, 193-208, (1989).

Cao, C.-X. et al. "Stacking Ionizable Analytes in a Sample Matrix with High Salt by a Transient Moving Chemical Reaction Boundary Method in Capillary Zone Electrophoresis", *Anal. Chem.* 74, 4167-4174 (2002).

Chen, Z. et al. "Chemically Modified chiral monolithic Silica Column Prepared by a Sol-Gel Process for Enantiomeric Separation by Micro High-Performanc Liquid Chromatography", *J. Chromatogra.*, 942, 83-91 (2002).

Chien, R.-L. et al. "Sample Stacking of an Extremely Large Injection Volume in High-Performance Capillary Electrophoresis", *Anal. Chem.*, 64, 1046-1050 (1992).

Chien, R.-L. et al. "On-Column Sample Concentration Using Field Amplification in CZE", *Anal. Chem.*, 64, 489A-496A (1992).

Chun, M.-S. et al. "Protein Analysis with Large Volume Sample Stacking with an Electrosmotic Flow Pump: A Potential Approach for Proteomics", *Microchem. J.*, 70, 247-253 (2001).

Church, M. N. et al. "Transient Isotachophoretic-Electrophoretic Separations of Lanthanides with Indirect Laser-Induced Fluorescence Detection", *Anal. Chem.*, 70, 2475-2480 (1998).

Cifuentes, A. et al. "Capillary Isoelectric Focusing of Erythropoietin Glycoforms and its Comparison with Flat-bed Isoelectric Focusing and Capillary Zone Electrophoresis", *J. Chromatogra.*, 830, 453-463 (1999).

Clarke, N. J. et al. "Capillary Isoelectric Focusing-Mass Spectrometry: Analysis of Protein Mixtures from Human Body Fluids", *Biomed. Chromatogr.*, 16, 287-297 (2002).

Clifford, A.A., "Introduction to Supercritical Fluid Extraction in Analytical Science," *Supercritical Fluid Extraction and its Use in Chromatographic Sample Preparation*, S.A. Westwood, Ed., Blackie Academic & Professional, Glasgow, 1-38 (1993).

Collinson, M. M. et al. "Sol-gels and Electochemistry", *Analytical Chemistry*, 72, 702A-709A (2000).

Coulibaly, K. et al. "An overview of Solid-Phase Extraction of Food Flavor Compounds and Chemical Residues", *Food Rev. Int.*, 12, 131-151 (1996).

Deng, Y. et al. "Chip-Based Quantitative Capillary Electrophoresis/ Mass Spectrometry Determination of Drugs in Human Plasma", *Anal. Chem.*, 73, 1432-1439 (2001).

Ettre, L.S., "Performance of Open Tubular Columns as a Function of Tube Diameter and Liquid Phase Film Thickness", *Chromatographia*, 18, 477-488 (1984).

Ettre, L.S. et al., *Basic Relationships of Gas Chromatography*, Advanstar, Cleveland, OH, 1-34 (1993).

(56) References Cited

OTHER PUBLICATIONS

Ferioli, V. et al., "High-Performance Liquid Chromatography of Dihydroxyacetone as its bis-2,4-Dinitrophenylhydrazone Derivative," *Chromatographia*, 41, 61-65 (1995).

Furton, K.G. et al., "The Use of Solid-Phase Microextraction-Gas Chromotagraphy in Forensic Analysis," *Journal of Chromatographic Science*, 38, 297-306 (2000).

Guo, Y. et al. "A Stationary Phase for Open Tubular Liquid Chromatography and Electrochromatography Using Sol-Gel Technology", *Anal. Chem.*, 67, 2511-2516 (1995).

Hamlet, C. et al., "Novel Sol-Gel Dendrimer Coatings for Ultra-Trace Environmental Analysis by Capillary Microextraction Coupled to Gas Chromatography", *5th International Symposium on Advances in Extraction Technologies*, St. Pete Beach, FL (Mar. 5-7, 2003).

Hartmann, H. et al., "Trace Determination of Pesticides in Water by Coated Capillary Micro Extraction (CCME) and Reversed-Phase High Performance Liquid Chromatography", *Fresenius Environmental Bulletin*, 7, 96-103 (1998).

Haruvy, Y. et al., "Sol-Gel Replication of Microoptical Elements and Arrays", *Chem. Mater.*, 9, 2604-2615 (1997).

Hayes, J.D. et al., "Sol-Gel Open Tubular ODS Columns with Reversed Electroosmotic Flow for Capillary Electrochromatography", *Anal. Chem.*, 73, 987-996 (2001).

Hayes, J.D. et al., "Sol-Gel Monolithic Columns with Reversed Electroosmotic Flow for Capillary Electrochromatography", *Anal. Chem.*, 72, 4090-4099 (2000).

Hayes, J.D. et al., "Sol-Gel Chemistry-Based Ucon-Coated Columns for Capillary Electrophoresis", *J. Chromatogr. B*, 695, 3-13 (1997).

Hayes, J.D. et al., "Sol-Gel Process Mediated Advanced Column Technology for Microcolumn Separations," *18th International Symposium on Capillary Chromatography*, 1, 496-504 (1996).

Hiraoka, A. et al. "One-Step Capillary Isoelectric Focusing of th Proteins in Cerebrospinal Fluid and Serum of Patients with Neurological Disorders", *J. Chromatogr. A*, 961, 147-153 (2002).

Hjertén, S. et al. "Adaptation of the Equipment for High-Performance Electrophoresis to Isoelectric Focusing", *J. Chromatogr.*, 346, 265-270 (1985).

Huang, M. et al. "Charged Surface Coatings for Capillary Electrophoresis", *J. Microcol.*, 5, 199-205 (1993).

Janák, K. et al., "Static Coating of Capillary Columns by Means of Liquefied Gases", *Journal of High Resolution Chromatography & Chromatography Communications*, 8, 843-847 (1985).

Kameoka, J. et al. "A Polymeric Microfluidic Chip for CE/MS Determination of Small Molecules", *Anal. Chem.*, 73, 1935-1941 (2001).

Kataoka, H. et al., "Automated In-Tube Solid-Phase Microextraction Coupled with Liquid Chromatography/Electrospray Ionization Mass Spectrometry for the Determination of β-Blockers and Metabolites in Urine and Serum Samples", *Anal. Chem.*, 71, 4237-4244 (1999).

Kataoka, H. et al. "Simple and Rapid Determination of Amphetamine, Methamphetamine, and Their Methylenedioxy Derivatives in Urine by Automated In-Tube Solid-Phase Microextraction Coupled with Liquid Chromatograpy-Electrospray Ionization Mass Spectrometry", *Journal of Analytical Toxicology*, 24, 257-265 (2000).

Kim, J-B. et al. "On-line Sample Concentration in Micellar Electrokinetic Chromatography Using Cationic Surfactants", *J. Chromatogr. A*, 916, 123-130 (2001).

Koivusalmi, E. et al., "Quantitative RP-HPLC Determination of Some Aldehydes and Hydroxyaldehydes as Their 2,4-Dinitrophenylhydrazone Derivatives", *Anal. Chem.*, 71, 86-91 (1999).

Lichtenberg, J. et al. "Sample Preconcentration by Field Amplification Stacking for Microchip-Based Capillary Electrophoresis", *Electrophoresis*, 22, 258-271 (2001).

Liu, Q. et al. "Poly(diallyldimethylammonium chloride) as a Cationic Coating for Capillary Electrophoresis", *J. Chromatogr. Sci.*, 36, 126-130 (1997).

Locke, S. et al. "Techniques for the Optimization of Proteomic Strategies Based on Head Coumn Stacking Capillary Electrophoresis", *Anal. Chem.*, 72, 2684-2689 (2000).

Lee, M. L. et al. "Fused Silica Capillary Column Technology for Gas Chromatography", *J. Chromatog. Sci.*, 22, 136-142 (1984).

Lopez-Avila, V. et al. "Evaluation of Soxtec Extraction Procedure fo Extacting Organic Compounds form Soils and Sediments", *J. AOAC International*, 76, 864-880 (1993).

MacKenzie, J. D. et al. "Hybrid Organic-Inorganic Materials, The Sol-Gel Approach" in *ACS Symposium Series*, 585, 226-236 (1995).

Majors, R. E. "Liquid Extraction Techniques for Sample Preparation", *LC GC International*, 10, 93-101 (1997).

Malik, A. et al., "Advanced Sol-gel Column Technology for Condensed-phase Microseparations", 25 Proc. *19th International Symposium on Capillary Chromatography and Electrophoresis*, Wintergreen, VA, USA, 54-55 (May 18-22, 1997).

Markides, K.E. et al., "Deactivation of Fused Silica Capillary Columns with Phenylhydrosiloxanes," *Journal of High Resolution Chromatography and Chromatography Communications*, 8, 378-384 (1985).

Martin, A. J. P. et al. "Displacement Electrophoresis", *Proc. Roy. Soc. Lond. A.*, 316, 493-514 (1970).

Minnich, M. M. et al. "Extraction Methods for Recovery of Volatile Organic Compounds from Fortified Dry Soils", *J. AOAC International*, 79, 1198-1204 (1996).

Mukherjee, S.P., "Supercritical Drying in Structural and Microstructural Evolution of Gels: A Critical Review", *Ultrastructure Processing of Advanced Ceramics*, J.D. MacKenzie and D.R. Ulrich, eds., John Wiley & Sons, New York—Chichester—Brisbane—Toronto—Singapore, 747-758 (1988).

Nawrocki, J. "Silica Surface Controversies, Strong Adsorption Sites Their Blockage and Removal. Part I", *Chromatogaphia*, 31, 177-205 (1991).

Novak, B. M. "Hybrid Nanocomposite Materials—Between Inorganic Glasses and Organic Polymers", *Advanced Materials*, 5, 422-433 (1993).

Núñez, O. et al. "Sample Stacking with Matrix Removal for the Determination of Paraquat, Diquat and Difenzoquat in Water by Capillary Electrophoresis", *J. Chromatogr. A*, 912, 353-361 (2001).

Oesterhelt, G. et al., "Analyse von Hydroxypivalaldehyd als Trimethylsilylderivat des Oxims mittels Gas-Chromatographie", *Fresenius Z. Anal. Chem.*, 321, Abstract (1985).

Ogden, M.W. et al., "Characterization of Fused-Silica Capillary Tubing by Contact Angle Measurements," *Journal of Chromatography*, 354, 7-18 (1986).

Palkar, V.R., "Sol-Gel Derived Nanostructured γ-Alumina Porous Spheres as an Adsorbent in Liquid Chromatography", *NanoStructured Materials*, 11, 369-374 (1999).

Pawliszyn, J., "Theory of Solid-Phase Microextraction," *Journal of Chromatographic Science*, 38, 270-278 (1999).

Palmer, J. et al. "Stacking Neutral Analytes in Capillary Electrokinetic Chromatographic with High-Salt Sample Matrixes", *Anal. Chem.*, 72, 1941-1943 (2000).

Palmer, J. et al. "A Universal Concept for Stacking Neutral Analytes in Micellar Capillary Electrophoresis", *Anal. Chem.*, 71, 1679-1687 (1999).

Palmer, J. et al. "Electrokinetic Injection for Stacking Neutral Analytes in Capillary and Microchip Electrophoresis", *Anal. Chem.*, 73, 725-731 (2001).

Quirino, J. P. et al. "Approaching a Million-Fold Sensitivity Increase in Capillary Electrophoresis with Direct Ultraviolet Detection: Cation-Selective Exhaustive Injection and Sweeping", *Anal. Chem.* 72, 1023-1030 (2000).

Quirino, J. P. et al. "Sweeping of Analyte Zones in Electrokinetic Chromatography", *Anal. Chem.* 71, 1638-1644 (1999).

Quirino, J. P. et al. "Exceeding 5000-Fold Concentration of Dilute Analytes in Micellar Electrokinetic Chromatography", *Science*, 282, 465-468 (1998).

Quirino, J. P. et al. "On-line Concentration of Neutral Analytes for Micellar Electrokinetic Chromatography II. Reversed Electrode Polarity Stacking Mode", *J. Chromatogr. A*, 791, 255-267 (1997).

Quirino, J. P. et al. "Sweeping with an Enhanced Electric Field of Neutral Analyte Zones in Electrokinetic Chromotography", *J. High Resol. Chromatogr.*, 22, 367-372 (1999).

(56) References Cited

OTHER PUBLICATIONS

Quirino, J. P. et al. "On-line Concentration of Neutral Analytes for Micellar electrokinetic Chromatography 5. Field-Enhanced Sample Injection with Reversed Migrating Micelles," *Anal. Chem*, 70, 1893-1901 (1998).

Quirino, J. P. et al. "On-line Concentration of Neutral Analytes for Micellar Electrokinetic Chromatography I. Normal Stacking Mode", *J. Chromatogr. A*, 781, 119-128 (1997).

Reighard, T.S. et al., "Bridging the Gap Between Supercritical Fluid Extraction and Liquid Extraction Techniques: Alternative Approaches to the Extraction of Solid and Liquid Environmental Matrices," *Critical Reviews in Analytical Chemistry*, 26, 61-99 (1996).

Righetti, P. G. et al. "Study of haptoglobin-hemoglobin Complexes by Titration Curves, Capillary Electrophoresis and Capillary Isoelectric Focusing", *J. Chromatogr. A*, 767, 255-262 (1997).

Rosenfeld, J. "Gas Chromatography Profiling in Biomedical Investigations" in *Chemical Analysis: Gas Chromatography*, Clement, R. E. (ed.), 111, 181-215 (1990).

Rotzsche, H., "Chemically Bonded Stationary Phases," Chapter 6 In: *Stationary Phases in Gas Chromatography*, Elsevier, Amsterdam, 1991.

Schomburg, G. et al., "Alkylpolysiloxane Glass Capillary Columns Combining High Temperature Stability of the Stationary Liquid and Deactivation of the Surface: Thermal Treatment of Dealkalinized Glass Surfaces by the Stationary Liquid Itself," *Chromatographia*, 12, 651-660 (1979).

Shen, Y. et al. "High-Efficiency Capillary Isoelectric Focusing of Peptides", *Anal. Chem.*, 72, 2154-2159, (2002).

Shende, C. et al. "Sol-Gel Poly(ethylene Glycol) Stationary Phase for High-Resolution Capillary Gas Chromatography", *Anal. Chem.*, 75, 3518-3530 (2003).

Shihabi, Z. K. "Stacking in Capillary Zone Electrophoresis", *J. Chromatogr. A.*, 902, 107-117 (2000).

Shihabi, Z. K. "Stacking and Discontinuous Buffers in Capillary Zone Electrophoresis", *Electrophoresis*, 21, 2872-2878 (2000).

Shihabi, Z. K. "Transient Pseudo-Isotachophoresis for Sample Concentration in Capillary Electrophoresis", *Electrophoresis*, 23, 1612-1617 (2002).

Shihabi, Z. K. et al. "Insulin Stacking in Capillary Zone Electrophoresis", *J. Chromatogr. A.*, 807, 129-133 (1998).

Soderquist, A., Office Action for U.S. Appl. No. 09/763,419, dated Jul. 2, 2003.

Spanik, I. et al. "Use of Full-Column Imaging Capillary Isoelectric Focusing for the Rapid Determination of the Operating Conditions in the Preparitive-Scale Continuous Free Flow Isoelectric Focusing Separation of Enantiomers", *J. Chromatogr. A.*, 960, 241-246 (2002).

Stark, F.O. et al., "The Interactions Between Trialkylsilanes and E-Glass or Aerosil Surfaces: Reactions of Trimethylsilanol, Trimethylchlorosilane, and Hexamethyldisilazane," *Journal of Physical Chemistry*, 72, 2750-2754 (1968).

Strausbauch, M. A. et al. "Mechanism of Peptide Separation by Solid Phase Extraction Capillary Electrophoresis at Low pH", *Anal. Chem.*, 68, 306-314 (1996).

Sumpter, S.R. et al. "Static Coating of 5 to 50 µm I.D. Capillary Columns for open Tubular Column Chromatography", *J. Chromatogr.*, 517, 503-519 (1990).

Sun, P. et al. "Chitosan Coated Capillary with Reserved Electroosmotic Flow in Capillary Electrophoresis for the Separation of Basic Drugs and Proteins", *J. Microcol. Sep.*, 6, 403-407 (1994).

Toussaint, B. et al. "Enantiomeric Separation of Clenbuterol by transient Isotachophoresis-capillary zone Electrophoresis-UV Detection New Optimization Technique for Transient Isotachophoresis", *J. Chromotogr. A.* 173-180 (2000).

Tu, C. et al. "Determination of Nitrate in Seawater by Capillary Zone Electophoresis with Chloride-Induced Sample Self-Stacking", *J. Chromatogr. A.*, 966, 205-212 (2002).

Van Der Vlis, E. et al., "Combined Liquid-Liquid Electroextraction and Isotachophoresis as a Fast On-line Focusing Step in Capillary Electrophoresis," *J. Chromatogr. A*, 687, 333-341 (1994).

Veraart, J. B. et al. "At-Line Solid-Phase Extraction Coupled to Capillary Electrophoresis: Determination of Amphoteric Compounds in Biological Samples", *J. High Resol. Chromatogr.*, 22, 183-187 (1999).

Vorotilov, K.A. et al., "ORMOSIL Films: Properties and Microelectronic Applications," *Journal of Sol-Gel Science and Technology*, 8, 581-584 (1997).

Wang, D. et al., "Sol-Gel Column Technology for Single-Step Deactivation, Coating, and Stationary-Phase Immobilization in High-Resolution Capillary Gas Chromatography", *Anal. Chem.*, 69, 4566-4576 (1997).

Wang, D. et al., "Preparation and GC Performance of Sol-Gel Technology-Based Open Tubular Columns," *18th International Symposium on Capillary Chromatography*, 1, 505-513 (1996).

Wang, Z. et al., "High-Performance Polyethylene Glycol-Coated Solid-Phase Microextraction Fibers Using Sol-Gel Technology," *J. Chromatogr. A*, 893, 157-168 (2000).

Wei, W. et al. "One-Step Concentration of Analytes Based on Dynamic Change in pH in Capillary Zone Electrophoresis", *Anal. Chem.*, 74, 934-940 (2002).

Welsh, T. et al., "The Thermal Immobilization of Hydroxy-Terminated Silicone Phases in High-Temperature-Silylated Glass Capillaries: A Study of Reaction Mechanisms," *Journal of High Resolution Chromatography*, 14, 153-159 (1991).

Wercinski, S.A.S. et al., "Solid Phase Microextraction Theory," Chapter 1 In: *Solid Phase Microextraction: A Practical Guide*, S.A.S. Wercinski, Ed., Marcel Dekker, Inc., New York, (1999).

Wilkes, G.L. et al.,"'Ceramers': Hybrid Materials Incorporating Polymeric/Oligomeric Species Into Inorganic Glasses Utilizing a Sol-Gel Approach," *Polymer Preprints*, 26, 300-302 (1985).

Woolley, C. L. et al. "Deactivation of Fused Silica Capillary Columns with Polymethylhydrosiloxanes", *J. High Resol. Chromatogr./ Chromatogr. Comm.*, 7, 329-332 (1984).

Wu, J. et al., "Polypyrrole-Coated Capillary Coupled to HPLC for In-Tube Solid-Phase Microextraction and Analysis of Aromatic Compounds in Aqueous Samples," *Anal. Chem.*, 73, 55-63 (2001).

Wu, J. et al., "Polypyrrole-Coated Capillary In-Tube Solid Phase Microextraction Coupled with Liquid Chromatography-Electrospray Ionization Mass Spectrometry for the Determination of β-Blockers in Urine and Serum Samples," *J. Microcolumn Separations*, 12, 255-266 (2000).

Wu, J. et al., "Speciation of Organoarsenic Compounds by Polypyrrole-Coated Capillary In-Tube Solid Phase Microextraction Coupled with Liquid Chromatography/Electrospray Ionization Mass Spectrometry," *Analytical Chimica Acta*, 424, 211-222 (2000).

Yang, H. et al. "Sample Stacking in Laboratory-on-a-chip Devices", *J. Chromatogr. A.*, 924, 155-163 (2001).

Zapf, A. et al., "GC Analysis of Organic Acids and Phenols Using On-Line Methylation with Trimethylsulfonium Hydroxide and PTV Solvent Split Large Volume Injection," *J. High Resol. Chromatogr.* 22, 83-88 (1999).

Zeng, Z. et al., "Solid-Phase Microextraction Using Fused-Silica Fibers Coated with Sol-Gel-Derived Hydroxy-Crown Ether," *Analytical Chemistry*, 73, 2429-2436 (2001).

Zhang, J. et al., "Development of the Personal Aldehydes and Ketones Sampler Based upon DNSH Derivatization on Solid Sorbent," *Environ. Sci. Technol.*, 34, 2601-2607 (2000).

Zhang, Z. et al., "Solid-Phase Microextraction," *Analytical Chemistry*, 66, 884A-853A (1994).

Mayer, *Journal of Chromatography A* 917, 219-226 (2001).

Dulay et al., "Preparation and Characterization of Monolithic Porous Capillary Columns Loaded with Chromatographic Particles", *Anal. Chem.*, 1998, pp. 5103-5107, vol. 70.

Aerts. A. et al. "Preparation, evaluation, and comparison of wide bore (320 µm) and narrow bore (50 µm) cyanosilicone-coated capillary columns for gas chromatography" *J. High Res. Chrom. & Chrom. Comm.*, 1986, 9:49-56.

Blum, W. "Preparation of inert glass capillary columns coated with UCON 50 HB-5100. An attempt to rediscover industrially produced α, ω-polyethylene/polypropyleneglycol ethers as stationary phases in capillary gas chromatography" *J. High Res. Chrom. & Chrom. Comm.*, 1987, 10:32-38.

(56) References Cited

OTHER PUBLICATIONS

Farbrot, A. et al. "Polymerized stationary phases in 12 to 50 μm open tubular fused silica columns for LC and GC" *J. High Res. Chrom. & Chrom. Comm.*, 1986, 9:117-119.

Hetem, M. et al. "Deactivation with polymethylhydrosiloxane. A comparative study with capillary gas chromatography and solid-state $^{29}$Si nuclear magnetic resonance spectroscopy" *J. of Chrom.*, 1989, 477:3-24.

Röder, W. et al. "Chiral SFC-separations using polymer-coated open tubular fused silica columns. Comparison of enantiomeric selectivity in SFC and LC using the same stationary phase of the Pirkle type" *J. High Res. Chrom. & Chrom. Comm.*, 1987, 10:665-667.

Steenackers, D. and Sandra, P. "Capillary GC on 50 micrometer I.D. columns coated with thick films. Theory and selected practical results" *J. High Res. Chrom.*, 1995, 18:77-82.

Traitler, H. "A cold silanization method for preparation of medium polarity capillary columns" *J. High Res. Chrom. & Chrom. Comm.*, 1983, 6:60-63.

Blomberg, L. et al. "In situ synthesis of highly thermostable, non-extractable, methysilicone gum phases for glass capillary gas chromatography" Journal of Chromatography, 1979, pp. 81-88, vol. 168.

Breadmore, M.C. et al. "On-Capillary Ion-Exchange Preconcentration of inorganic Anions in Open-Tubular Capillariy Electrochromatography with Elution Using Transient-Isotachophoretic Gradiesnts. 2. Characterization of the Isotachophoretic Gradient" Anal. Chem., Feb. 15, 2001, pp. 820-828, vol. 73, No. 4.

Breadmore, M.C. et al. "On-Capillary Ion-Exchange Preconcentration of Inorganic Anions Using Open-Tubular Capillaries Followed by Elution with a Transient-Isotachophoretic Gradient" The Analyst Communication, 2000, pp. 799-802, vol. 125.

Breadmore, M.C. et al. "On-Column Ion-Exhange Preconcentration of Inorgainic Anions in Open Tubular Capillary Electrochromatography with Elution Using Transiant-Isotachophoretic Gradieants. 3. Implementation and Method Development" Anal. Chem., May 1, 2002, pp. 2112-2118, vol. 74, No. 9.

Capelli, L. et al. "'Tunable' positive negative surface charges on a capillary wall: exploiting the immobiline chemistry" J. Biochem. Biophys. Methods, 1996, 32:109-124.

Chong et al. "Sol-Gel Coating Technology for the Preparation of Solid-Phase Microextraction Fiber of Enhanced Thermal Stability" Analytical Chemistry 1997, 69, 3889-3898.

Denton, K.A. and Harris, R. "High-performance capillary electrophoretic separation of human serum albumin using a neutral coated capillary" J. Chrom. A, 1995, 704:335-341.

Faramawy, S. et al. "Surface-modified silica gels as solid stationary phases in gas chromatography" Surface and Coatings Tech., 1997, 90:53-63.

Farkas, P. et al. "Interface adsorption and reproducibility of retention indices in glass capillary columns with dimethylpolysiloxane stationary phases cross-linked by γ-irradiation" Journal of Chromatography, 1989, pp. 251-261, vol. 471.

Gilges, M. et al. "Capillary zone electrophoresis separations of basic and acidic proteins using poly(vinyl alcohol) coatings in fused silica capillaries" Anal. Chem., 1994, 66:2038-2046.

Horka, M. et al. "Influence of the capillary dimensions on the performance of the preconcentration technique based on parallel current chromatography" J. Chrom. A, 1997, 791:163-176.

Horvath, J. and Dolnik, V. "Polymer wall coatings for capillary electrophoresis" Electrophoresis, 2001, 22:644-655.

Huang, X. et al. "Spectroscopic probing of mixed-mode adsorption of Ru(bpy)3 2+ to silica" Anal. Chem., 1996, 68:4119-4123.

Jennings, W. et al. "The Open Tubular Column" in Analytical Gas Chromatography, 1997, pp. 30-48, Academic Press, San Diego, CA.

Kohler, J. and Kirkland, J.J. "Improved silica-based column packings for high-performance liquid chromatography" J. Chrom., 1987, 385:125-150.

Kohr, J. and Engelhardt, H. "Characterization of quartz capillaries for capillary electrophoresis" J. Chrom. A, 1993, 652:309-316.

Kominar, R.J. "The preparation and testing of a fused-silica gas chromatography capillary column" J. Chem. Edu., 1991, 68:A249-A255.

Lipkowitz, K.B. et al. "Explanation of where and how enantioselective binding takes place on permethylated β-cyclodextrin, a chiral stationary phase used in gas chromatography" J. Am. Chem. Soc., 1997, 119:600-610.

Lipsky, S.R. et al. "Role of surface groups in affecting the chromatographic performance of certain types of fused-silica glass capillary column" Journal of Chromatography, 1984, pp. 129-142, vol. 289.

Madani, C. et al. "New method for the preparation of highly stable polysiloxane-coated glass open-tubular capillary columns and application to the analysis of hormonal steroids" Journal of Chromatography, 1976, pp. 161-169, vol. 126.

Madani, C. et al. "High resolution glass capillary columns with chemically bonded stationary phases: Application to the gas chromatographic analysis of sterols and steroids in biological extracts" Journal of the American Oil Chemist's Society, 1981, pp. 63-70, vol. 58.

Malik, A. et al. "Simple method for the preparation of highly efficient polymer-coated capillary electrophoresis columns" Journal of Microcolumn Separations, 1993, pp. 119-125, vol. 5.

Malik; Advances in Sol-Gel Based Columns for Capillary Electrochromatography; Sol-Gel Open-Tubular Columns; Electrophoresis; p. 3973-3992; 2002.

Moseley, M.A. and Pellizzari, E.D. "Polysiloxane deactivated fused silica capillaries containing immobilized stationary phases" J. of HRC & CC, 1982, 5:472-475.

Narang, P. et al. "Sol-gel-derived fluorinated stationary phase for open tubular electrochromatography" Journal of Chromatography A, 1997, pp. 65-72, vol. 773.

Nawrocki, J. "How strongly do silanols interact with hydrocarbon solutes in gas chromatography?" J. Chrom., 1986, 362:117-120.

Nawrocki, J. "The silanol group and its role in liquid chromatography" J. Chrom. A, 1997, 779:29-71.

Ogden, M.W. et al. "Characterization of fused-silica capillary tubing by contact angle measurements" Chemical Abstracts, 1986, vol. 104, abstract 236559f.

Ogden, M.W. et al. "Hydrothermal treatment of fused silica capillary columns" J. of HRC & CC, 1985, 8:326-331.

Rodriguez, S.A. et al. "Study of the Solution in the Synthesis of a Sol-Gel Composite Used as a Chromatographic Phase" Chem. Mater., 1999, pp. 754-762, vol. 11.

Schutjes, C.P.M. et al. "Deactivation and Coating of Non-Polar 50 μm I.D. Capillary Columns", J. Chromatogr., 1983, 279:49-57.

Schwartz, R.D. et al. "Sol-coated capillary adsorption columns for gas chromatography" Analytical Chemistry, 1963, pp. 496-499, vol. 35.

Tock, P.P.H. et al. "Performance of porous silica layers in open-tubular columns for liquid chromatography" Journal of Chromatography, 1989, pp. 95-106, vol. 477.

Woolley, C.L. et al. "Static coating of phenyl and biphenyl polysiloxane stationary phases on small-diameter capillary columns" Journal of High Resolution Chromatography and Chromatography Communications, 1988, pp. 113-118, vol. 11.

Woolley, C.L. et al. "Deactivation of Fused-Silica Capillary Columns with Polymethylhydrosiloxanes" Journal of Chromatography, 1986, pp. 23-34, vol. 367.

Zeng, Z.R. et al. "Preparation and characteristics of two new GC stationary phases-dihydroxy crown ether containing polysiloxane" Chromatographia, 1992, pp. 85-90, vol. 34.

\* cited by examiner

HIGH EFFICIENCY SOL-GEL GAS CHROMATOGRAPHY COLUMN

CROSS-REFERENCE TO RELATED APPLICATIONS

This application is a continuation of U.S. application Ser. No. 10/471,388, filed Mar. 8, 2004 now abandoned, which is a U.S. national stage application of international patent application No. PCT/US02/07163, filed Mar. 8, 2002, which claims the benefit of U.S. Provisional Application Ser. No. 60/274,886, filed Mar. 9, 2001.

BACKGROUND OF THE INVENTION

1. Technical Field

The present invention relates to analytical separation technology and more specifically towards gas chromatography separation systems based on sol-gel stationary phases having improved performance characteristics.

2. Background Art

The introduction of an open tubular column by Golay (Golay, M. J. E., et al.) about three decades ago, has revolutionized the analytical capability of gas chromatography (hereinafter "GC"). More specifically, capillary GC has matured into a separation technique that is widely used in various fields of science and industry (Altgelt, K. H., et al.; Clement, R. E.; Berezkin, V. G., et al.; and Tebbett, I.). Capillary GC is a separation technique in which the vapor phase of a sample in a gaseous, mobile phase passes through a capillary tube whose inner walls contain a thin film of an adsorbing or absorbing medium (i.e., stationary phase). Because of differential interactions of the sample components with the stationary phase, the individual components of the sample move through the column with different velocities. This leads to the physical separation of the sample components into individual chromatographic zones as they move down the column with their characteristic velocities. The separated components are detected instrumentally as they are eluted from the column. Contemporary technology for the preparation of open tubular columns is time-consuming. It consists of three major, individually executed steps (Poole, C. F., et al.): capillary surface deactivation (Woolley, C. L. et al.), static coating (Bouche, J. et al.), and stationary phase immobilization (Blomberg L. G.). Involvement of multiple steps in conventional column technology increases the fabrication time and is likely to result in greater column-to-column variation. The column deactivation step is critically important for the GC separation of polar compounds that are prone to undergo adsorptive interactions (e.g., with the silanol groups on fused silica capillary inner walls). In conventional column technology, deactivation is usually carried out as a separate step, and involves chemical derivatization of the surface silanol groups. Various reagents have been used to chemically deactivate the surface silanol groups (de Nijs; R. C. M., et al.; Schomburg, G. et al.; Blomberg, L. et al.; and Lee, M. L. et al.). Effectiveness of these deactivation procedures greatly depends on the chemical structure and composition of the fused silica surface to which they are applied.

Of special importance are the concentration and mode of distribution of surface silanol groups. Because the fused silica capillary drawing process involves the use of high temperatures (~2,000° C.), the silanol group concentration on the drawn capillary surface can initially be low due to the formation of siloxane bridges under high-temperature drawing conditions. During subsequent storage and handling, some of these siloxane bridges can undergo hydrolysis due to reaction with environmental moisture. Thus, depending on the postdrawing history, even the same batch of fused silica capillary can have different concentrations of the silanol groups that can also vary by the modes of their distribution on the surface.

Moreover, different degrees of reaction and adsorption activities are shown by different types of surface silanol groups (Lawrocki, J.). As a result, fused silica capillaries from different batches or even from the same batch but stored and/or handled under different conditions, cannot produce identical surface characteristics after being subjected to the same deactivation treatments. This makes surface deactivation a difficult procedure to reproduce. To overcome these difficulties, some researchers have used hydrothermal surface treatments to standardize silanol group concentrations and their distributions over the surface (Sumpter, S. R. et al.). This additional step however, makes the time consuming column making procedure even longer. Static coating is another time-consuming step in conventional column technology. A typical 30-m long column can require as much as ten hours or more for static coating. The duration of this step can vary depending on the length and diameter of the capillary, and the volatility of the solvent used.

To coat a column by the static coating technique, the fused silica capillary is filled with a stationary phase solution prepared in a low-boiling solvent. One end of the capillary is sealed using a high viscosity grease or by some other means (Abe, I. et al.), and the other end is connected to a vacuum pump. Under these conditions, the solvent begins to evaporate from the capillary end connected to the vacuum pump, leaving behind the stationary phase that becomes deposited on the capillary inner walls as a thin film. Stationary phase film of desired thickness could be obtained by using a coating solution of appropriate concentration that can be easily calculated through simple equations (Ettre, L. S. et al.).

In static coating, two major drawbacks are encountered. First, the technique is excessively time consuming, and not very suitable for automation. Second, the physically coated stationary phase film shows a pronounced tendency to rearrangements that can ultimately result in droplet formation due to Rayleigh instability (Bartle, K. D. et al.). Such a structural change in the coated films can serve as a cause for the deterioration or even complete loss of the column's separation capability.

To avoid these undesirable effects, static-coated stationary phase films need to be stabilized immediately after their coating. This is usually achieved by stationary phase immobilization through free radical cross-linking (Wright, B. W. et al.) that leads to the formation of chemical bridges between coated polymeric molecules of the stationary phase. In such an approach, stability of the coated film is achieved not through chemical bonding of the stationary phase molecules to the capillary walls, but mainly through an increase of their molecular size and consequently, through decrease of their solubility and vapor pressure.

Such an immobilization process has a number of drawbacks. First, polar stationary phases are difficult to immobilize by this technique (Yakabe, Y., et al.). Second, free radical cross-linking reactions are difficult to control to ensure the same degree of cross-linking in different columns with the same stationary phase. Third, cross-linking reactions can lead to significant changes in the polymer structure and chromatographic properties of the resulting immobilized polymer can significantly differ from those of the originally taken stationary phase (Blomberg L. G.). All these drawbacks add up to make column preparation by conventional techniques a task that is difficult to control and reproduce (Blomberg, L., et al.).

In order to overcome all of the above problems, a preparation of a GC capillary column including a tube structure and a deactivated surface-bonded sol-gel coating on a portion of the tube structure forming a stationary phase was disclosed and claimed in PCT Application PCT/US99/19113, published as WO 00/11463, to Malik et al. The invention disclosed therein is for a structure for forming a capillary tube, e.g., for gas chromatography, and a technique for forming such capillary tube. The capillary tube includes a tube structure and a deactivated surface-bonded sol-gel coating on a portion of the tube structure to form a stationary phase coating on that portion of the tube structure. The deactivated sol-gel stationary phase coating enables separation of analytes while minimizing adsorption of analytes on the separation column structure. This type of column was a significant advancement in the art, but it was recognized that certain improvements would greatly enhance the performance of the sol-gel coated column.

One area of improvement deals with baseline stability. A GC column is commonly operated under temperature-programmed conditions whereby the temperature of the column is increased with time. As the column temperature increases, the gas chromatography baseline rises because of column bleed caused due to the formation of volatile compounds from the stationary phase coating on the inner surface of the capillary column. In GC columns with polysiloxane-based stationary phases, the formation of volatile cyclic compounds is favored by the flexibility of the polysiloxane chains. One way to overcome or significantly reduce the column-bleeding problem is to reduce the flexibility of the polymeric structure of the GC stationary phase by incorporating phenyl rings in the polysiloxane backbone. This reduces the flexibility of polysiloxanes, and consequently, their ability to produce cyclic volatiles through rearrangements. The selection of the phenyl-containing reagent and the degree of substitution in the polysiloxane backbone are both critical, and care must be taken so that the stationary phase does not become too rigid. Otherwise, chromatographic properties of the polymer (especially the mass transfer properties) can be compromised. In an attempt to provide increased baseline stability, Mayer et al. used 1,4-bis(hydroxydimethylsilyl)benzene to incorporate a phenyl ring in the polydimethyldiphenylsiloxane structure by conducting its reaction with diphenylsilanediol at 110° C. for 48 hours. This non-sol-gel process however, is inconvenient for two reasons. First, the process is lengthy and carried out at elevated temperature. Second, the 1,4-bis(hydroxydimethylsiyl)benzene reagent used for the incorporation of the phenyl group provides a polymer structure where the phenyl ring is directly bonded to silicon atoms without any spacer groups and leads to a very rigid polymer affecting its mass transfer properties and chromatographic efficiency.

Accordingly, there is a need for an improved GC column having improved baseline stability, higher efficiency, and reduced conditioning time. Additionally, there is a need for a sol-gel GC column having desired stationary phase film thickness and improved retention characteristics that are capable of being fabricated into long columns. The present invention describes a sol-gel chemistry-based process that provides all of the above-mentioned desirable column characteristics through a simple procedure carried out under mild thermal conditions.

SUMMARY OF THE INVENTION

According to the present invention, there is provided a capillary column including a tube structure having inner walls and a sol-gel substrate coated on a portion of the inner walls of the tube structure to form a stationary phase coating on the inner walls. The sol solution used to prepare the sol-gel substrate has at least one baseline stabilizing reagent and at least one surface deactivation reagent. The resulting sol-gel substrate has at least one baseline stabilizing reagent residual and at least one surface deactivation reagent residual. The present invention further provides for a method of making a sol-gel solution for placement into a capillary column by mixing suitable sol-gel precursors, at least one sol-gel-active organic polymer or ligand, at least one baseline stabilization reagent to the sol-gel solution, at least one surface deactivation reagent, and at least one sol-gel catalyst.

BRIEF DESCRIPTION OF THE DRAWINGS

Other advantages of the present invention are readily appreciated as the same becomes better understood by reference to the following detailed description when considered in connection with the accompanying drawings wherein.

Figure 4A:
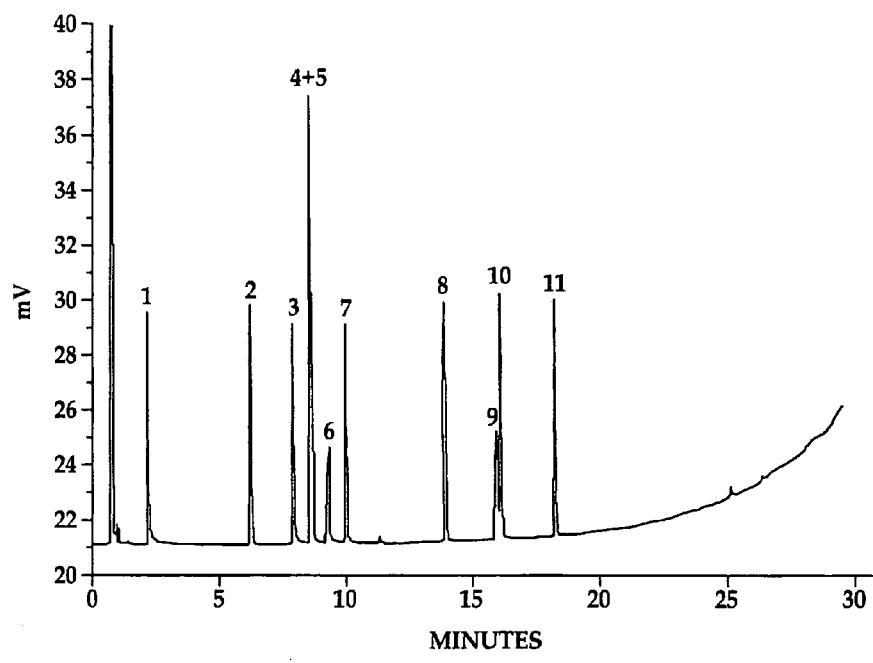
FIG. 4A. GC separation of Grob test mixture on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimethoxysilane, 1,1,1,3,3,3-hexamethyidisilazane, trifluoroacetic acid, ammonium fluoride but no bis(trimethoxysilylethyl)benzene, wherein the conditions are: 10-m×250-μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$ and with peaks (1)
Figure 4B:
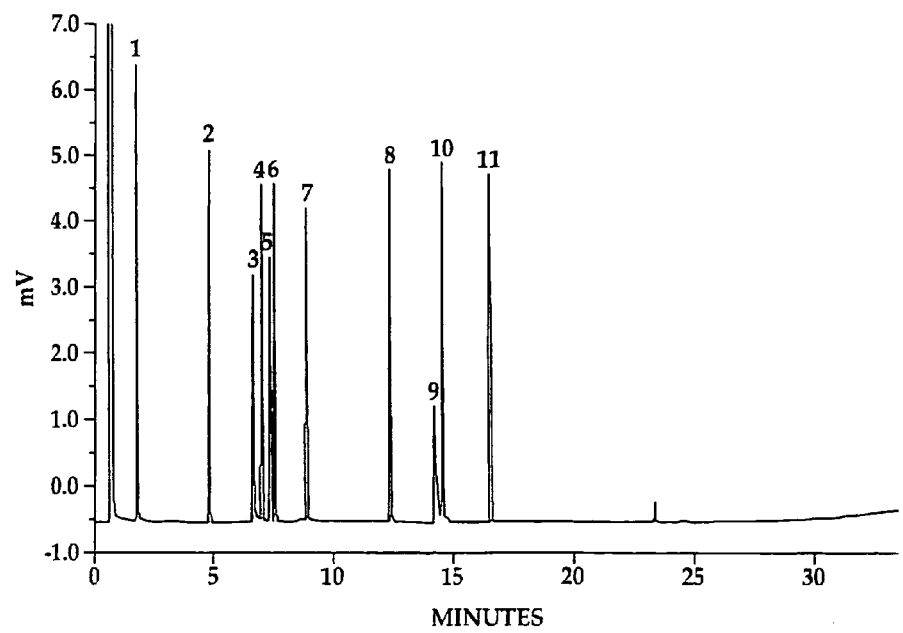
Figure 5A:
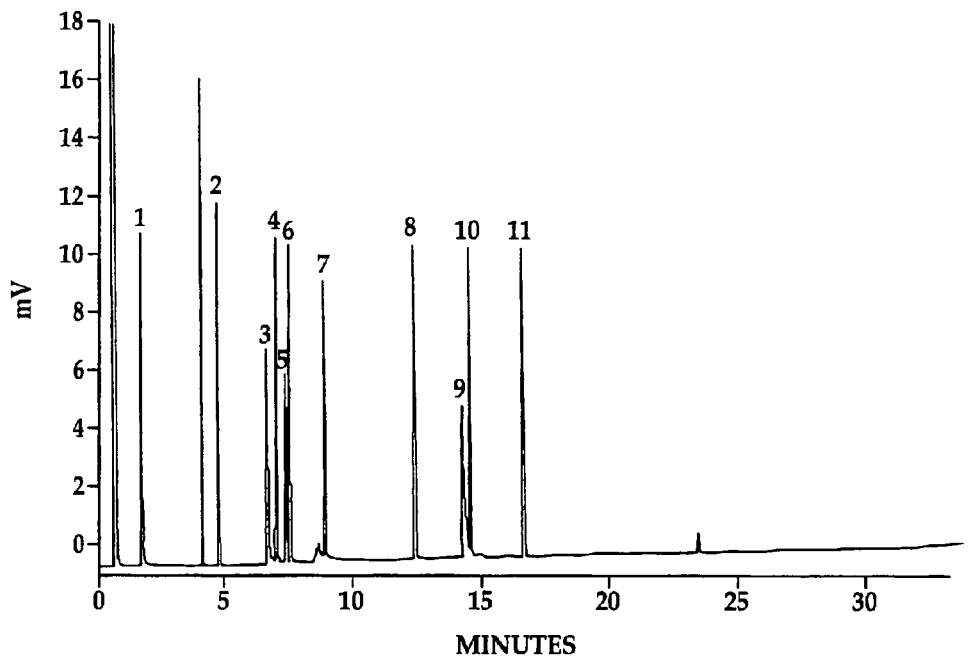
Figure 5B:
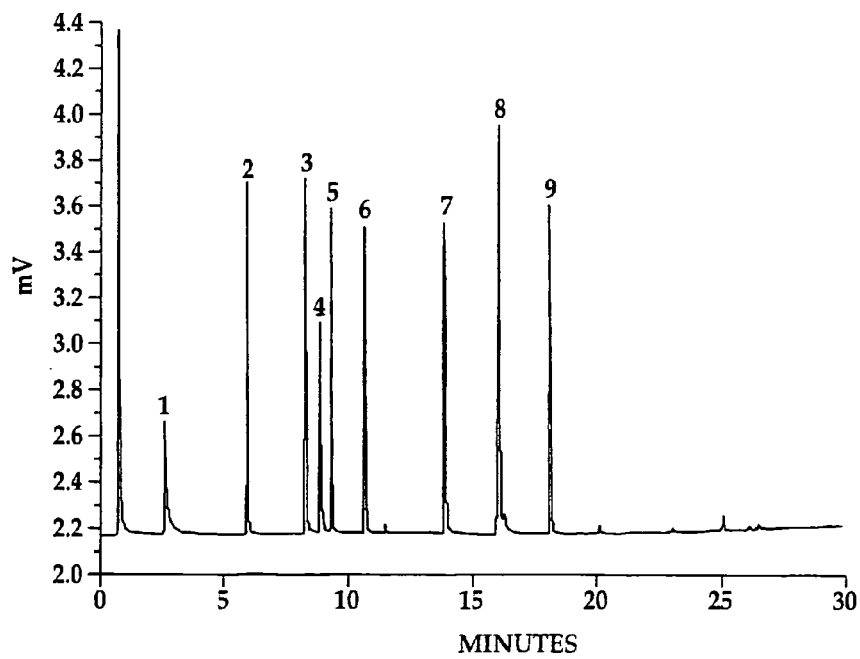
Figure 6:
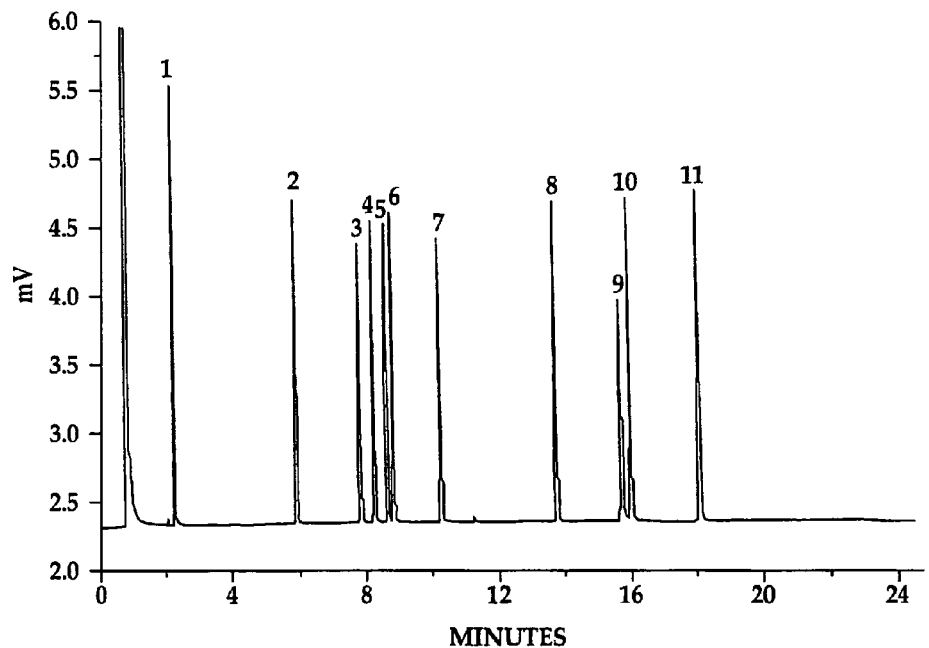
Figure 7:
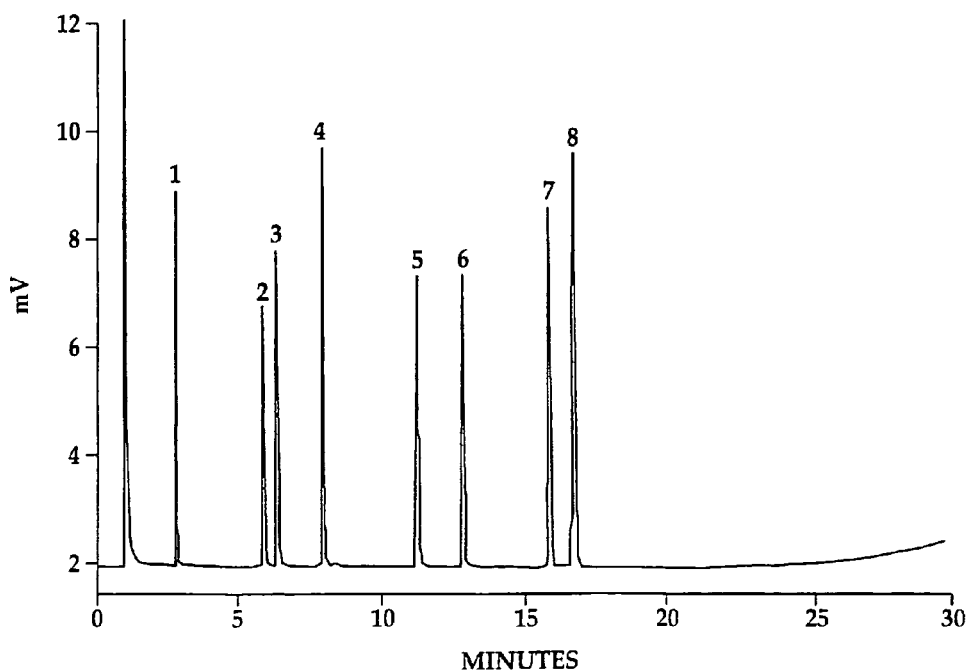
Figure 8:
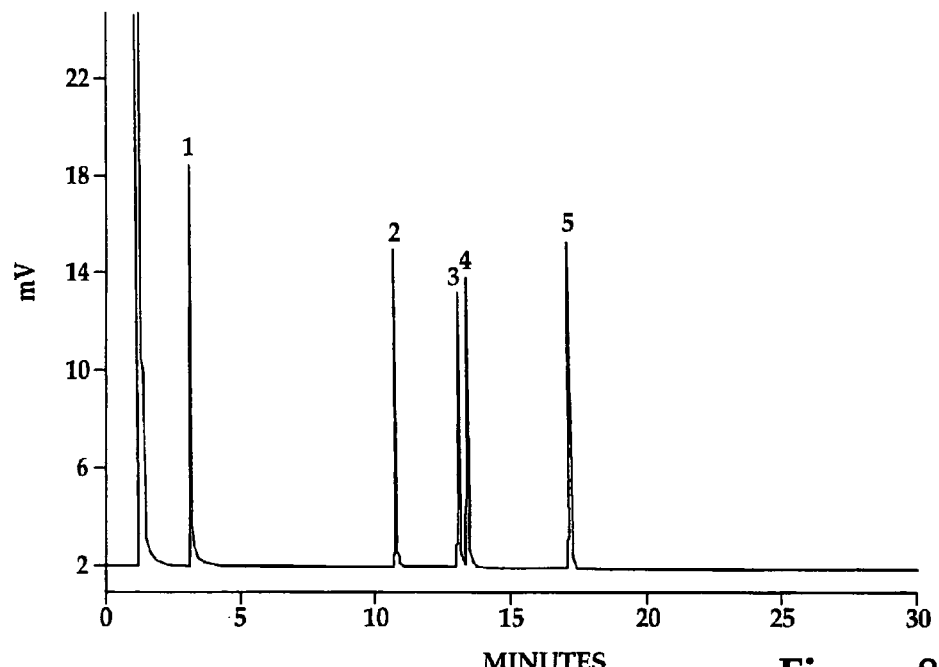
Figure 9:
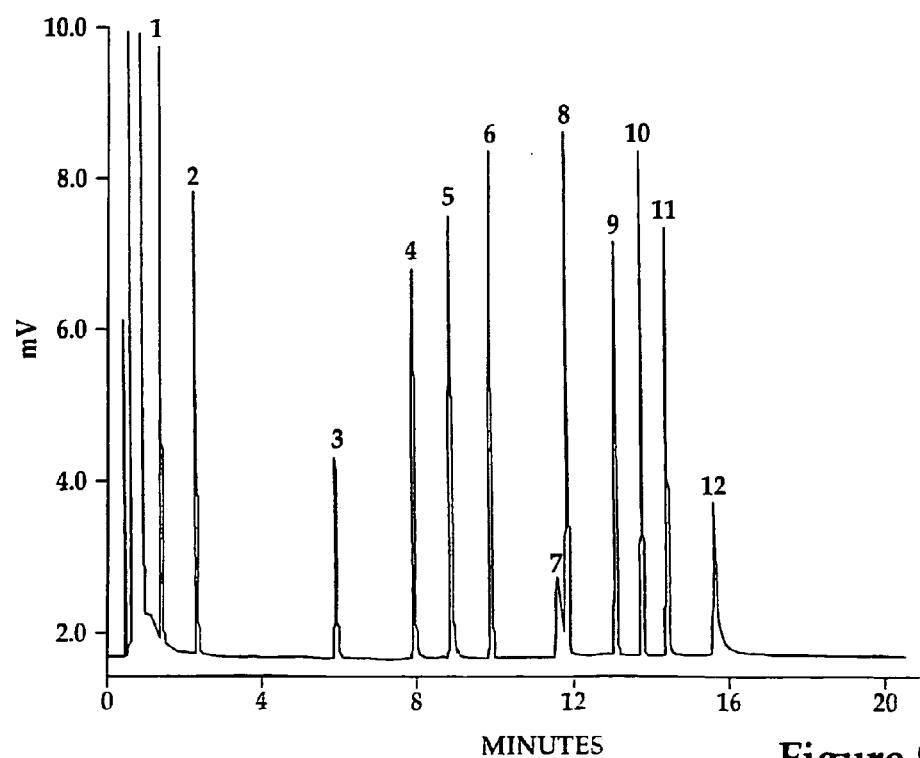
Figure 10:
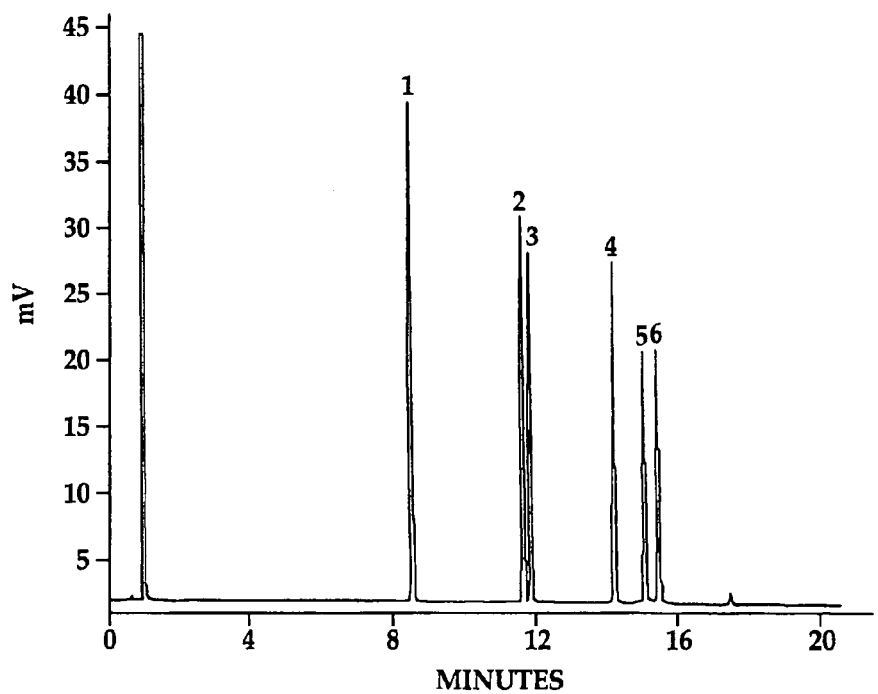
Figure 11:
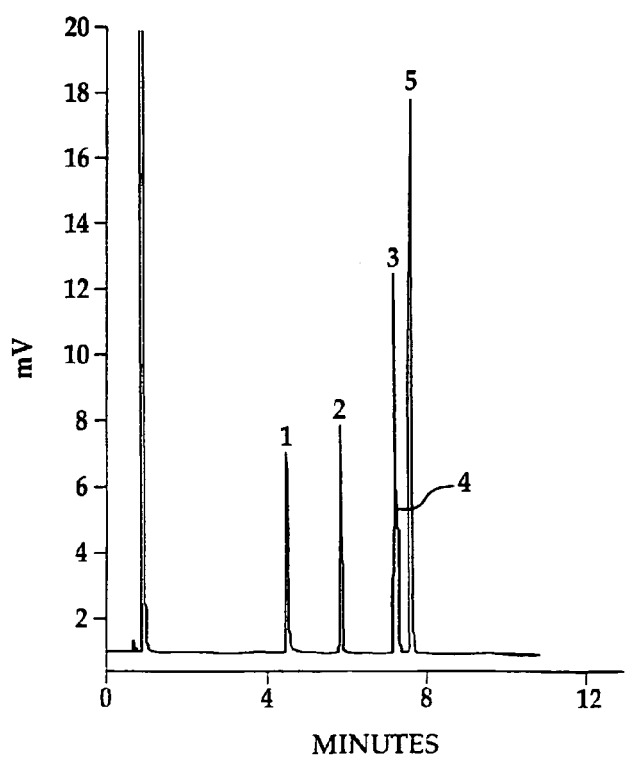
Figure 12:
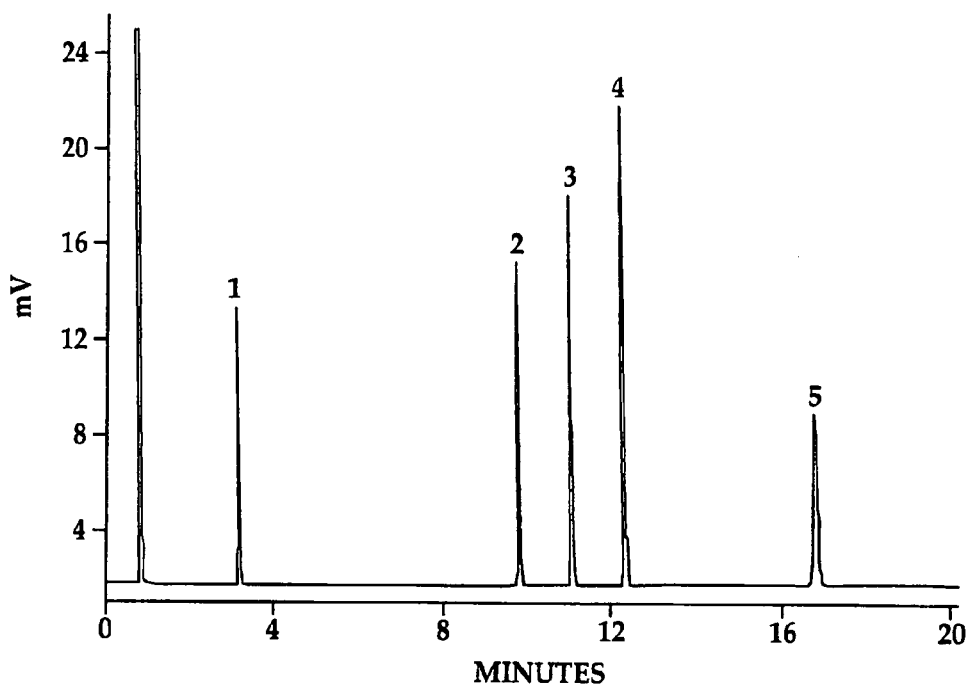
Figure 13:
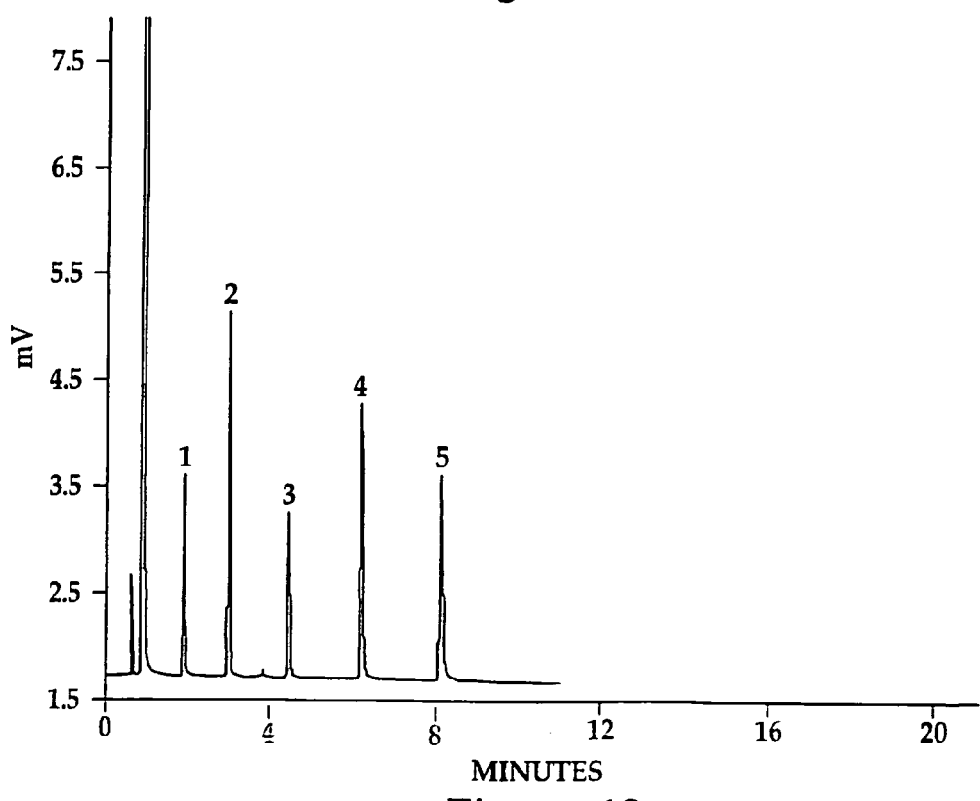
Figure 14:
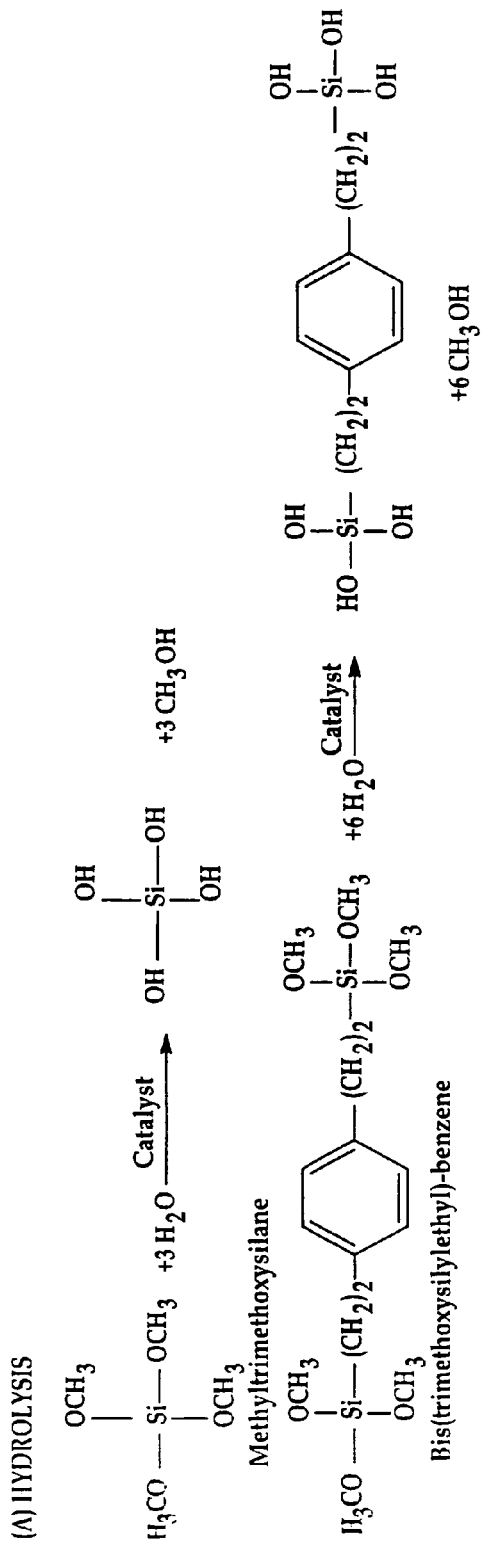
Figure 15:
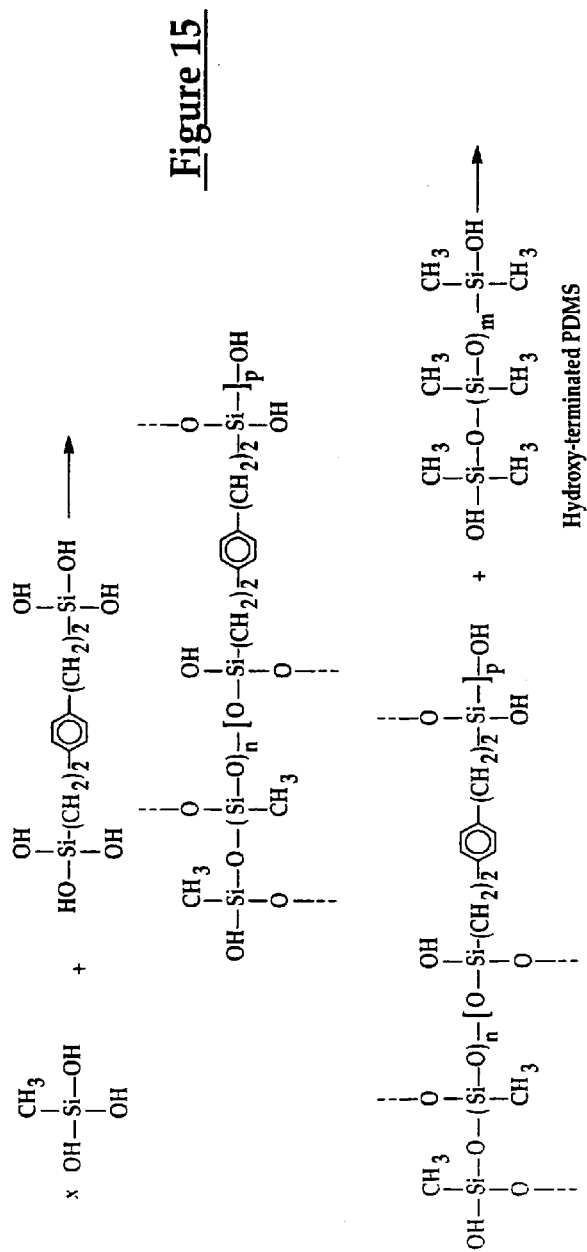
Figure 16:
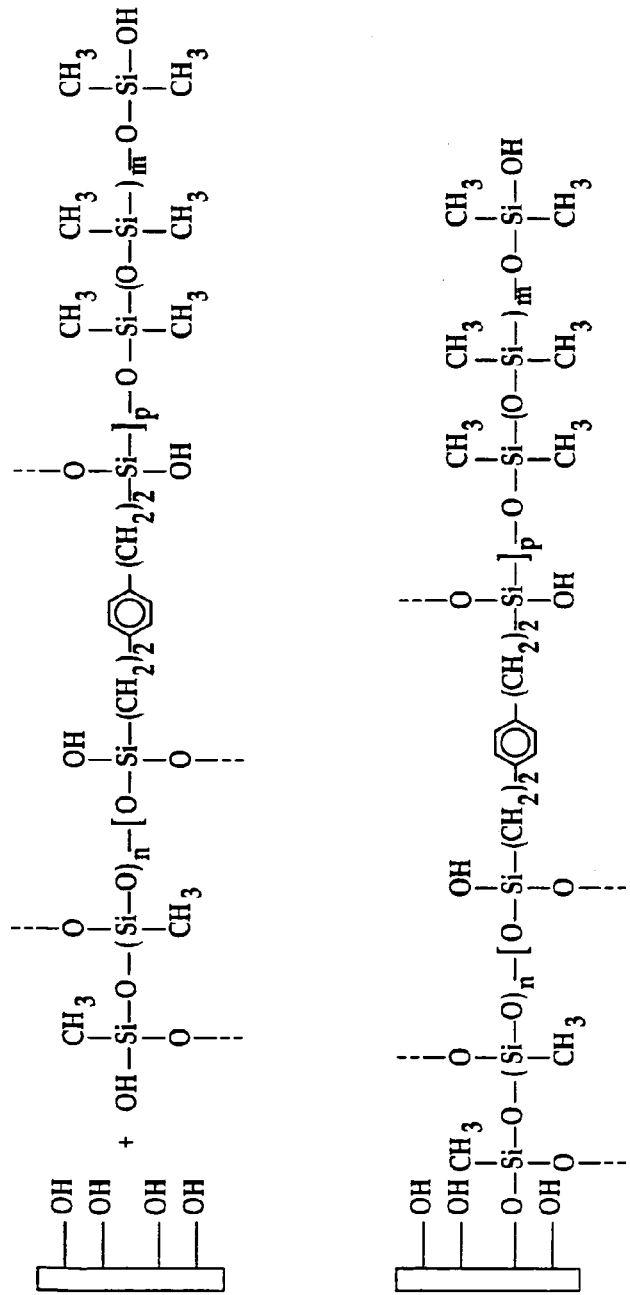
Figure 17:
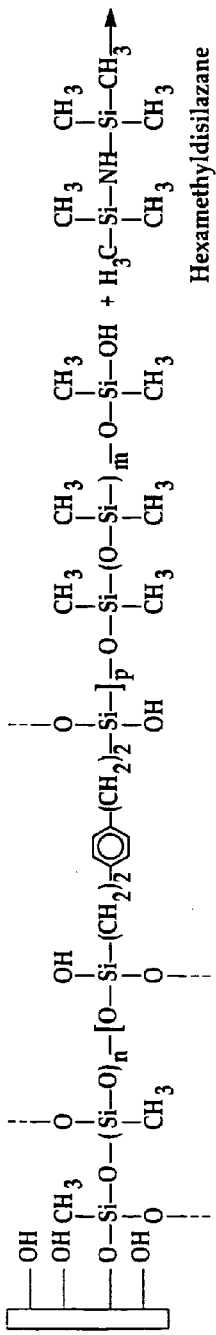
Figure 17:
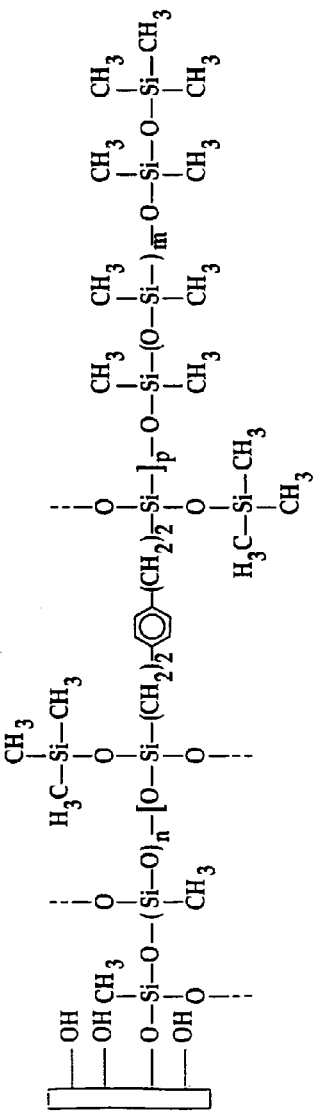
Figure 18:
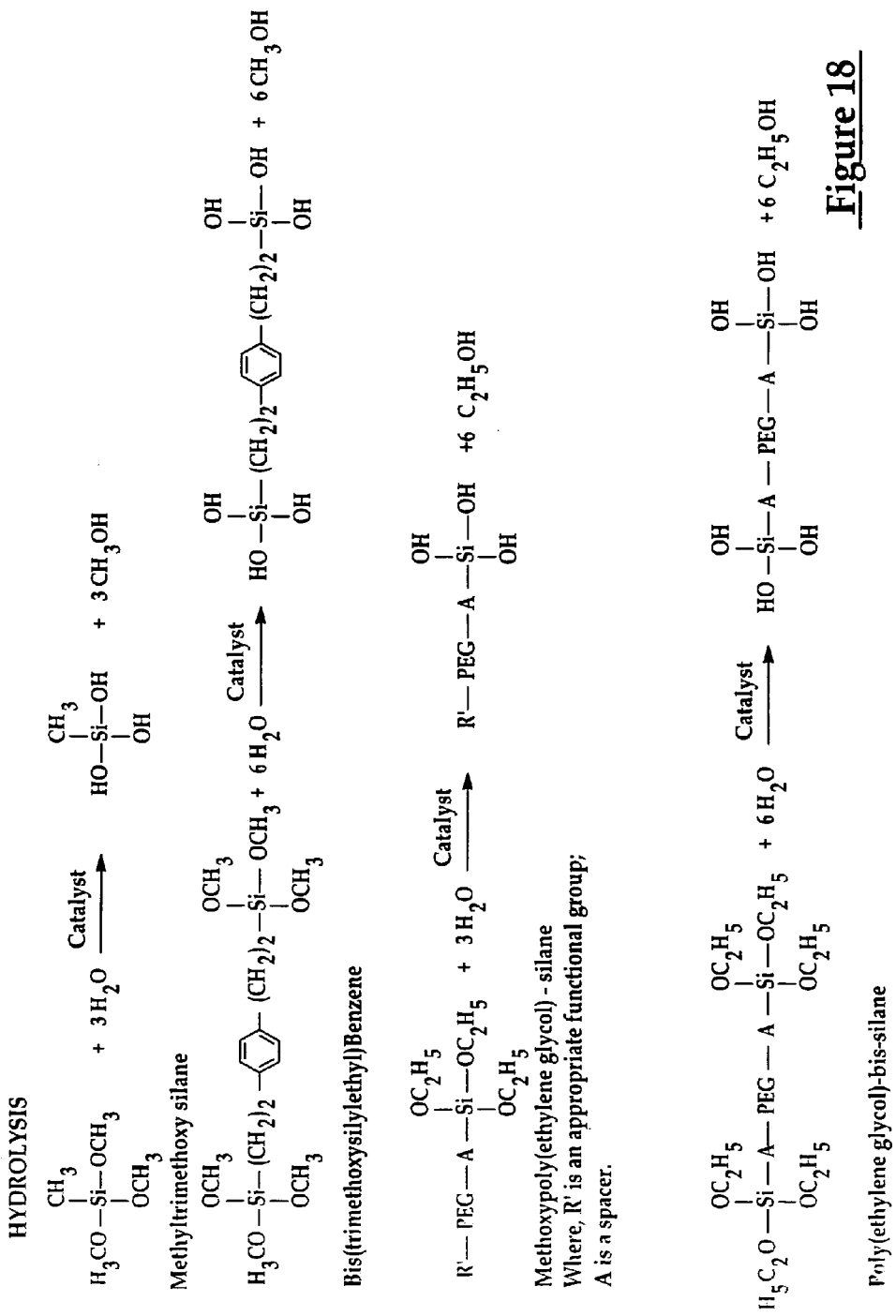
Figure 19:
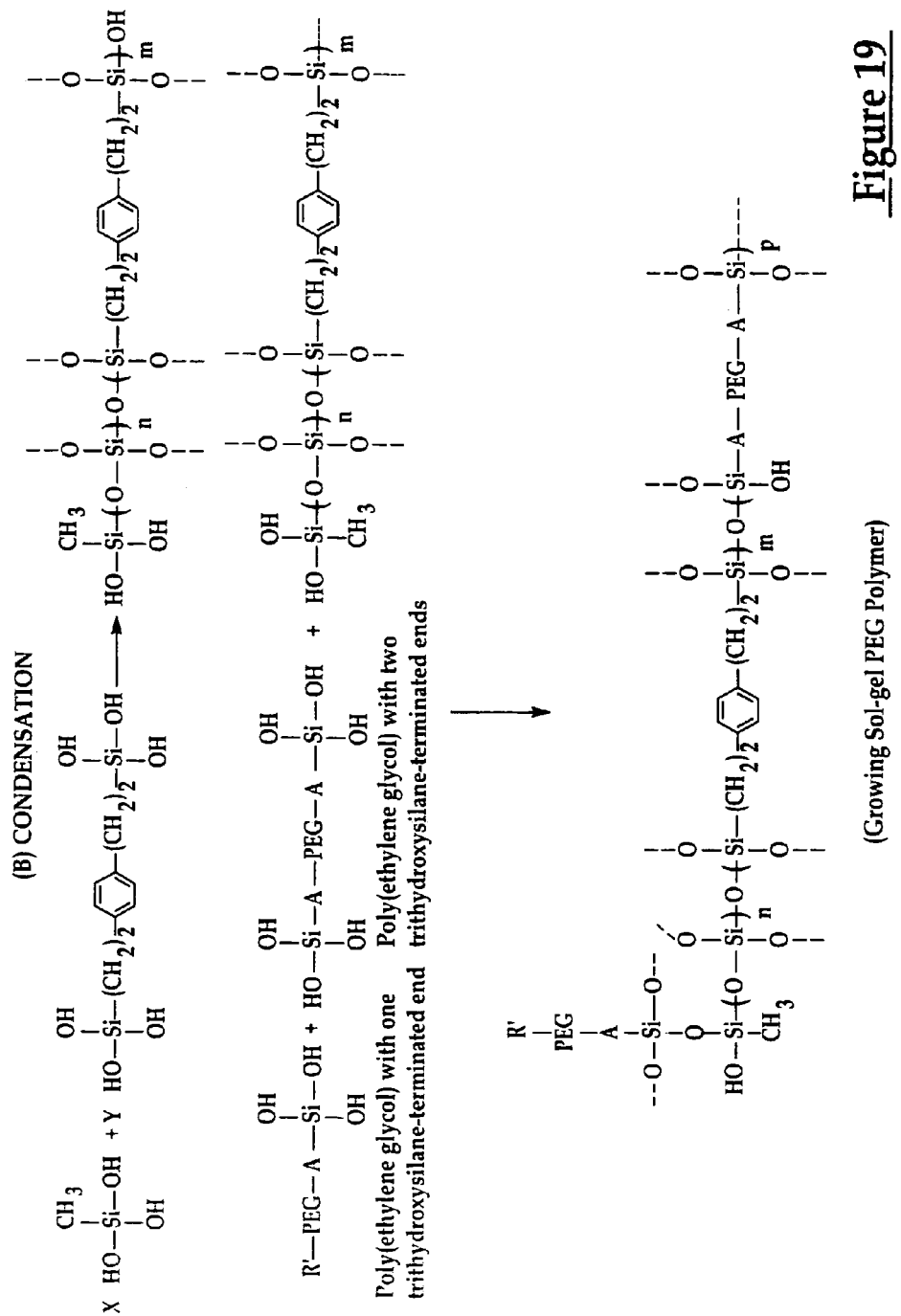
Figure 20:
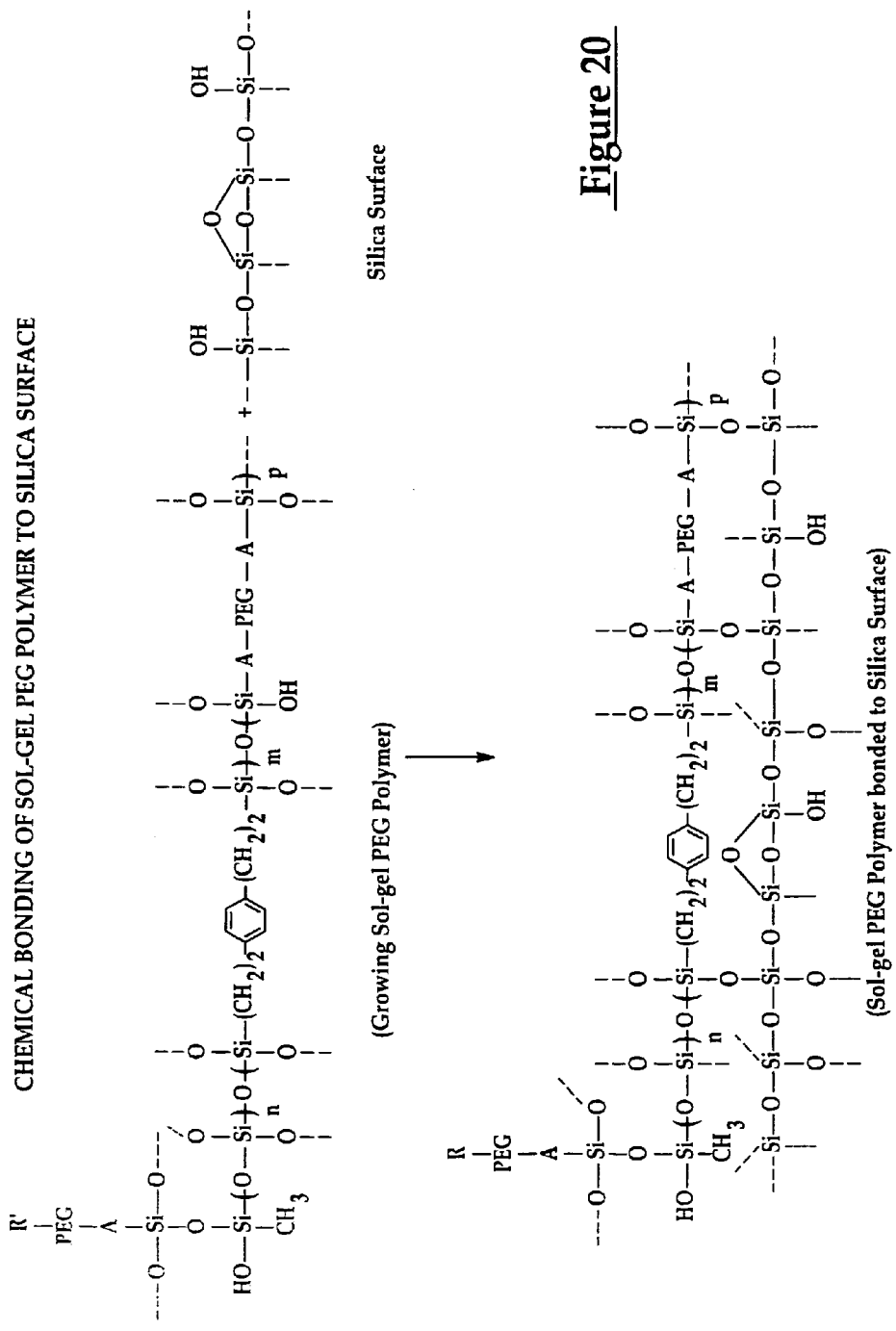
Figure 21:
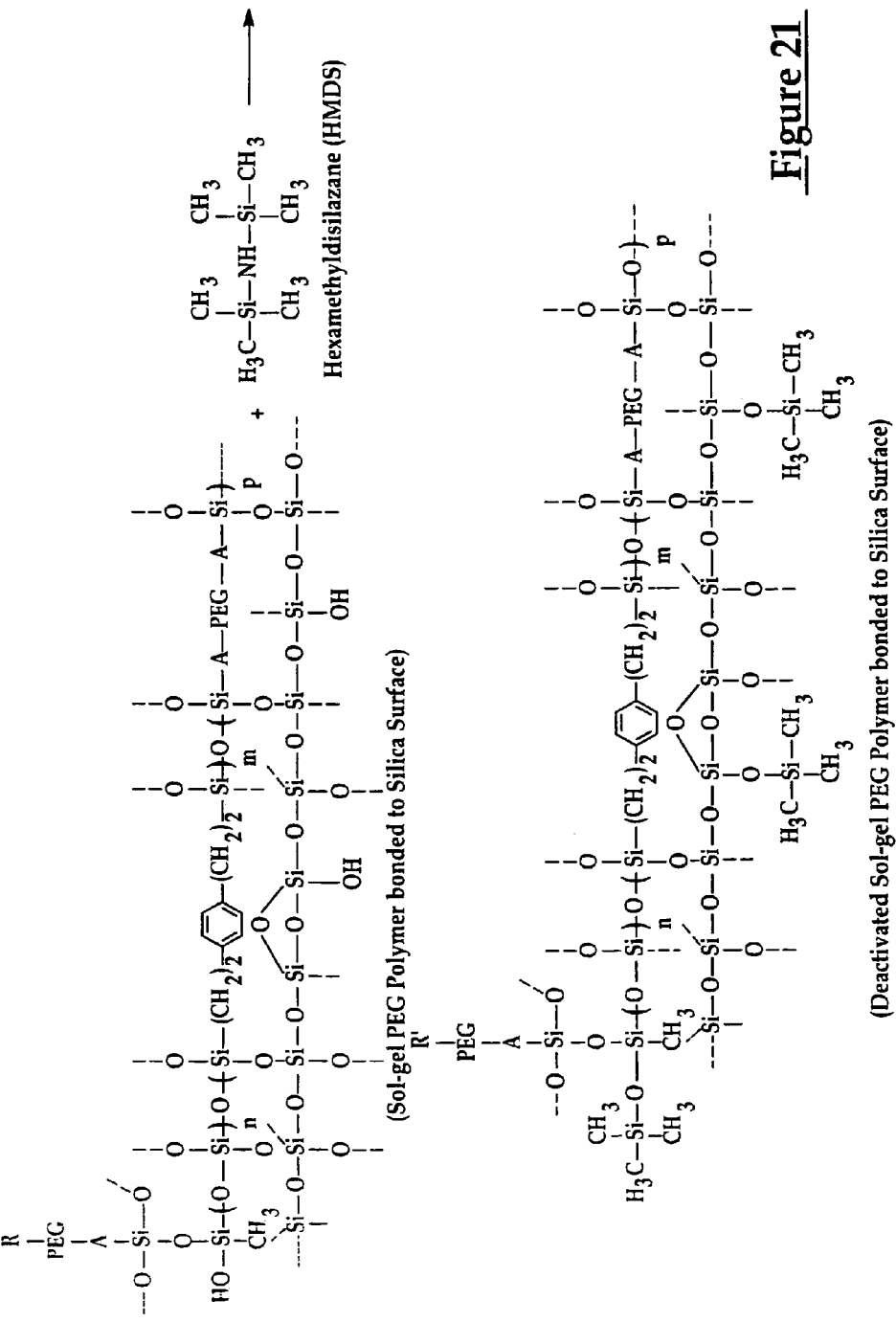
Figure 22A:
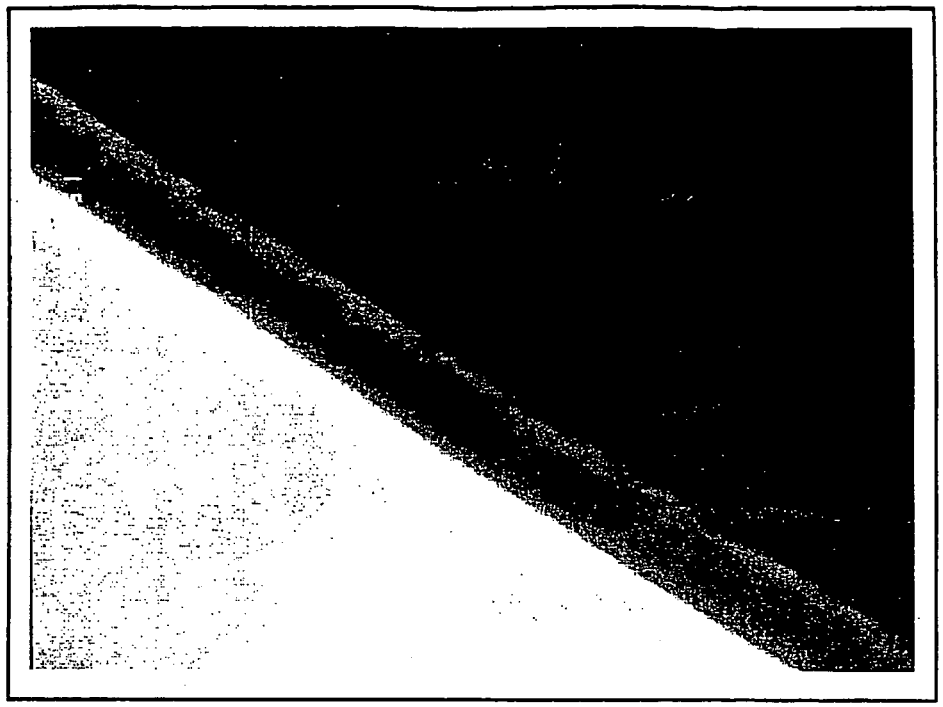
Figure 22B:
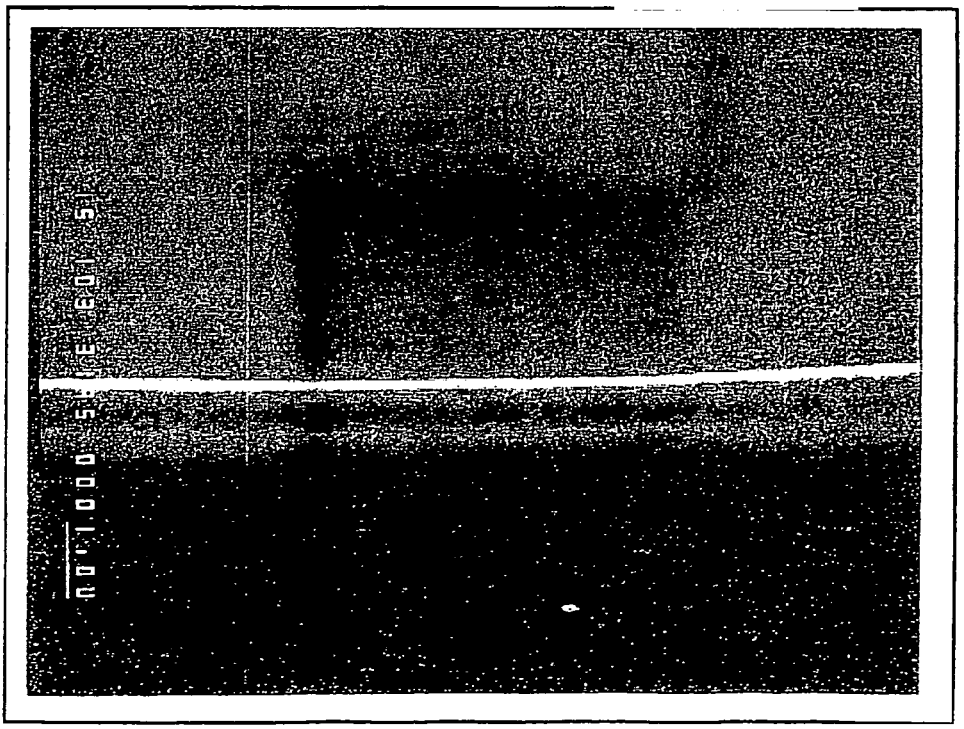

2,3-butanediol, (2) n-decane, (3) 1-octanol, (4) 2,6-dimethylphenol, (5) 1-nonanal, (6) n-undecane, (7) 2,6-dimethylaniline (8) methyl decanoate, (9) dicyclohexylamine, (10) methyl undecanoate, and (11) methyl dodecanoate;

FIG. 4B is a GC separation of Grob test mixture on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimethoxysilane, 1,1,1,3,3,3-hexamethyldisilazane, trifluoroacetic acid, ammonium fluoride, and bis(trimethoxysilylethyl)benzene with conditions being 10-m×250-μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$; and with peaks (1) 2,3-butanediol, (2) n-decane, (3) 1-octanol, (4) 2,6-dimethylphenol, (5) 1-nonanal, (6) n-undecane, (7) 2,6-dimethylaniline, (8) methyl decanoate, (9) dicyclohexylamine, (10) methyl undecanoate, and (11) methyl dodecanoate;

FIG. 5A is a GC separation of Grob test mixture on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimethoxysilane, trifluoroacetic acid, ammonium fluoride and bis(trimethoxysilylethyl)benzene and 1,1,1,3,3,3-hexamethyidisilazane, with conditions being 10-m×250-μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$, and with peaks (1) 2,3-butanediol, (2) n-decane, (3) 1-octanol, (4) 2,6-dimethylphenol, (5) 1-nonanal, (6) n-undecane, (7) 2,6-dimethylaniline, (8) methyl decanoate, (9) dicyclohexylamine, (10) methyl undecanoate, and (11) methyl dodecanoate;

FIG. 5B is a GC separation of Grob test mixture on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimthoxysilane, trifluoroacetic acid, ammonium fluoride and bis(trimethoxysilylethyl)benzene but no 1,1,1,3,3,3-hexamethyldisilazane, with conditions being 10-m×250-μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$, and peaks (1) 2,3-butanediol, (2) n-decane, (3) 1-octanol, (4) 2,6-dimethylphenol, (5) n-undecane, (6) 2,6-dimethylaniline, (7) methyl decanoate, (8) methyl undecanoate, and (9) methyl dodecanoate;

FIG. 6 is a GC separation of Grob test mixture on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimethoxysilane, 1,1,1,3,3,3-hexamethyidisilazane, trifluoroacetic acid, ammonium fluoride and bis(trimethoxsilylethyl)benzene, with conditions being 10-m×250-μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$; and with peaks (1) 2,3-butanediol, (2) n-decane, (3) 1-octanol, (4) 2,6-dimethylphenol, (5) 1-nonanal, (6) n-undecane, (7) 2,6-dimethylaniline, (8) methyl decanoate, (9) dicyclohexylamine, (10) methyl undecanoate, and (11) methyl dodecanoate;

FIG. 7 is a GC separation of PAHs on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimethoxysilane, 1,1,1,3,3,3-hexamethyldisilazane, trifluoroacetic acid, ammonium fluoride and bis(trimethoxysilylethyl)benzene with conditions being 10-m×250-μm-i.d. fused silica capillary column; stationary phase, sol-gel PDMS; carrier gas, helium; injection, split (100:1, 300° C.); detector, FID, 350° C., temperature programming from 80° C. at 6° C. minutes$^{-1}$ and with peaks (1) naphthalene, (2) acenaphthylene, (3) acenaphthylene, (4) fluorene, (5) phenanthrene, (6) o-terphenyl, (7) fluoranthene, and (8) pyrene;

FIG. 8 is a GC separation of aniline derivatives on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimethoxysilane, 1,1,1,3,3,3-hexamethyldisilazane, trifluoroacetic acid, ammonium fluoride and bis(trimethoxysilylethyl)benzene, with conditions being 10-m×250-μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$ and with peaks (1) pyridine, (2) N-methylaniline, (3) 2-ethylaniline, (4) 4-ethylaniline, (5) N-butylaniline;

FIG. 9 is a gas chromatogram demonstrating separation of a Grob test mixture on a sol-gel-coated PEG column, wherein the conditions are: 10-m×250-μm-i.d. fused silica capillary column; stationary phase, sol-gel polyethylene glycol (PEG); carrier gas, helium; injection, split (100:1, 300° C.); detector, FID, 350° C., temperature programming from 40° C. at 6° C. min$^{-1}$; and with peaks (1) n-decane, (2) n-undecane, (3) nonanal, (4) 2,3-butanediol, (5) 1-octane, (6) methyl decanoate, (7) dicylcohexylamine, (8) methyl undecanoate, (9) methyl dodecanoate, (10) 2,6-dimethylaniline, (11) 2,6-dimethylphenol, and (12) 2-ethylhexanoic acid;

FIG. 10 is a gas chromatogram illustrating separation of aniline derivatives on a sol-gel coated PEG column, wherein the conditions are: 10-m×250-μm-i.d. fused silica capillary column; stationary phase, sol-gel polyethylene glycol (PEG); carrier gas, helium; injection, split (100:1, 300° C.); detector, FID, 350° C.; temperature programming from 65° C. at 6° C. min$^{-1}$; and with peaks (1) N,N-dimethylaniline, (2) N-methylaniline, (3) N-ethylaniline, (4) 2-ethylaniline, (5) 4-ethylaniline, and (6) 3-ethylaniline;

FIG. 11 is a gas chromatogram illustrating separation of aldehydes on a sol-gel coated PEG column, wherein the conditions are: 10-m×250 μm-i.d. fused silica capillary column; stationary phase, sol-gel polyethylene glycol (PEG); carrier gas, helium; injection, split (100:1, 300° C.); detector, FID, 350° C.; C; temperature programming from 75° C. at 6° C. min$^{1}$; and with peaks (1) nonylaldehyde, (2) benzaldehyde, (3) o-otoulaldehyde, (4) m-toulaldehyde, and (5) p-toulaldehyde;

FIG. 12 is a gas chromatogram demonstrating separation of ketones on a sol-gel coated PEG column, wherein the conditions are: 10-m×250-μm-i.d. fused silica capillary column; stationary phase, sol-gel polyethylene glycol (PEG); carrier gas, helium; injection, split (100:1, 300° C.); detector, FID, 350° C.; temperature programming from 80° C. at 6° C. min$^{-1}$; and with peaks (1) 5-nonanone, (2) butyrophenone, (3) valerophenone, (4) hexanophenone, and (5) heptanophenone;

FIG. 13 is a gas chromatogram illustrating separation of alcohols on a sol-gel coated PEG column, wherein the conditions are: 10-m×250 µm-i.d. fused silica capillary column; stationary phase, sol-gel polyethylene glycol (PEG); carrier gas, helium; injection, split (100:1, 300° C.); detector, FID, 350° C.; temperature programming from 70° C. at 6° C. min$^{-1}$; and with peaks (1) butanol, (2) pentanol, (3) hexanol, (4) heptanol, and (5) octanol;

FIG. 14 is a schematic illustration of hydrolysis reactions involved in the preparation of sol-gel PDMS coated columns according to the present invention;

FIG. 15 is a schematic illustration of condensation reactions involved in sol-gel PDMS stationary phase of the present invention;

FIG. 16 is a schematic illustration of a condensation reaction of the present invention occurring on a fused silica capillary inner surface;

FIG. 17 is a schematic illustration of a deactivation of residual silanol groups using hexamethyldisilazane (HMDS);

FIG. 18 is a schematic illustration of hydrolysis reactions for the preparations of sol-gel PEG coated columns according to the present invention;

FIG. 19 is a schematic illustration of a condensation reaction of the present invention demonstrating the growth of a sol-gel PEG polymer (A is a spacer group);

FIG. 20 is a schematic illustration of a growing sol-gel PEG polymer being bonded to a silica surface;

FIG. 21 is a schematic illustration of a reaction of the sol-gel PEG polymer bonded to a silica surface with hexamethyldisilazane (HMDS) to form a deactivated sol-gel PEG polymer coating bonded to the silica surface;

FIG. 22 A is a scanning electron micrograph of a sol-gel PDMS coating on the inner surface of a fused silica capillary column (magnification 10,000×); and FIG. 22 B is a scanning electron micrograph of a sol-gel PEG coating on the inner surface of a fused silica capillary column (magnification 10,000×).

DETAILED DESCRIPTION OF THE INVENTION

Generally, the present invention is directed to a capillary column and to a method of making the capillary column, wherein the capillary column provides for a rapid and simple method for simultaneous deactivation, coating, and stationary phase immobilization in gas chromatography (hereinafter "GC"). To achieve this goal, a sol-gel chemistry-based approach to column preparation is provided that is a viable alternative to conventional GC column technology. The sol-gel column technology eliminates the major drawbacks of conventional column technology through chemical bonding of the sol-gel stationary phase molecules to an interfacial layer that evolves on the top of the original capillary surface. More specifically, the present invention provides for a sol-gel GC column having improved baseline stability, higher efficiency, and reduced conditioning time. The present invention further provides for a sol-gel GC column having desired stationary phase film thicknesses and improved retention characteristics that are capable of being fabricated into long columns as long as 30 meters or longer. The present invention is useful for capillary systems as well as any other chromatography system that employs the use of polysiloxane-based, PEG-based, and other types of stationary phases for separation.

The term "baseline stability" as used herein is defined as, but is not limited to, a state wherein the formation of volatile products due to the breakdown of the stationary phase at elevated temperatures is hindered or prevented. More specifically, baseline stability occurs when the stationary phase is prevented from rearrangement so that the formation of low molecular weight compounds is suppressed. This can be achieved through a reduction of polymer chain flexibility by introducing a rigid phenyl group into the polymer backbone.

The term "deactivation reagent" as used herein is defined as, but is not limited to, any reagent that reacts with the polar adsorptive sites (e.g., silanol groups) on the column inner surface or stationary phase coating, and thereby prevents the stationary phase coating within the column from adsorbing polar analytes. The adsorptive interaction of the stationary phase with polar analytes occurs because of the presence of silanol groups that are harmful to polar compounds desired to be analyzed.

The present invention has numerous applications and uses. Primarily, the present invention is useful in separation processes involving analytes including, but not limited to, hyrdocarbons, polycyclic aromatic hydrocarbons (PAHs), alcohols, aldehydes, ketones, phenols, fatty acids, fatty acid methyl esters, amines, and other analytes known to those of skill in the art. Accordingly, the present invention is useful in chemical, petrochemical, environmental, pharmaceutical applications, and other similar applications.

The present invention has various advantages over the prior art. The sol-gel chemistry-based novel approach to column technology is presented for high resolution capillary GC that provides a fast way of surface roughening, deactivation, coating, and stationary phase immobilization—all carried out in a single step. Unlike conventional column technology in which these procedures are carried out as individual, time-consuming, steps, the new technology can achieve all these just by filling a capillary with a sol solution of appropriate composition, and allowing it to stay inside the capillary for a controlled period, followed by inert gas purging and conditioning of the capillary. The new technology greatly simplifies the methodology for the preparation of high efficiency GC columns, and offers an opportunity to reduce the column preparation time at least by a factor of ten. Being simple in technical execution, the new technology is very suitable for automation and mass production. Columns prepared by the new technology provide significantly superior thermal stability due to direct chemical bonding of the stationary phase coating to the capillary walls. Enhanced surface area of the columns, as evidenced by SEM results, provides a sample-capacity advantage to the sol-gel columns. The new methodology provides excellent surface deactivation quality, which is either comparable with or superior to that obtained by conventional techniques. This is supported by examples of high efficiency separations obtained for polar compounds including free fatty acids, amines, alcohols, diols, phenols, aldehydes and ketones. The sol-gel column technology has the potential to offer a viable alternative to existing methods for column preparation in analytical microseparation techniques.

The present invention has numerous embodiments, depending upon the desired application. As described below, the formation of the various embodiments are intended for use in gas chromatography. However, due to the vast applicability of the present invention, the column and related methods thereof can be modified in various manners for use in other areas of analytical separation technologies. The principles of the present invention can also be used to form capillary columns for use in liquid chromatography, capillary electrochromatography, supercritical fluid chromatography, and as sample preconcentrators where a compound of interest is present in very small concentrations in a sample.

Figures 1, 2:
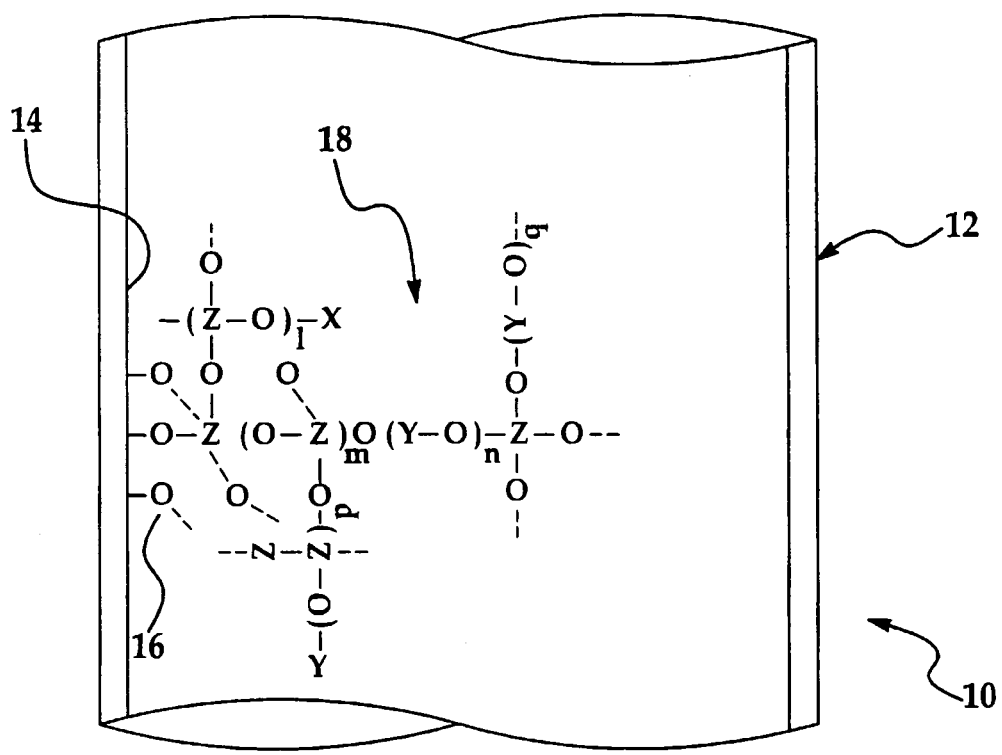
FIG. 1 is a longitudinal, cross-sectional view of an embodiment of a capillary column of the present invention.
FIG. 2 is drawing of an embodiment of the present invention, more specifically, a filling and purging device for the preparation of the capillary column of the present invention.

In one embodiment (FIG. 1), the present invention provides for a capillary column 10 including a tube structure 12 having inner walls 14 and a sol-gel substrate 16 coated on a portion of the inner walls 14 of the tube structure 12 to form a stationary phase coating 18 on the inner walls 14. The stationary phase coating 18 is created using at least one baseline stabilizing reagent and at least one surface deactivation reagent. The stationary phase coating 18 is bonded to the inner walls 14 of the tube structure 12. The surface-bonded sol-gel substrate 16 is applied to the inner walls 14 of the tube structure 12 by use of an apparatus as illustrated in FIG. 2 and the method described herein.

The tube structure 12 of the capillary column 10 can be made of numerous materials including, but not limited to alumina, fused silica, glass, titania, zirconia, polymeric hollow fibers, and any other similar tubing materials known to those of skill in the art. Typically, fused silica is the most convenient material used. Sol-gel chemistry in analytical microseparations presents a universal approach to creating advanced material systems including those based on alumina, titania, and zirconia that have not been adequately evaluated in conventional separation column technology. Thus, the sol-gel chemistry-based column technology has the potential to effectively utilize advanced material properties to fill this gap.

As for the sol-gel substrate, it has the formula:

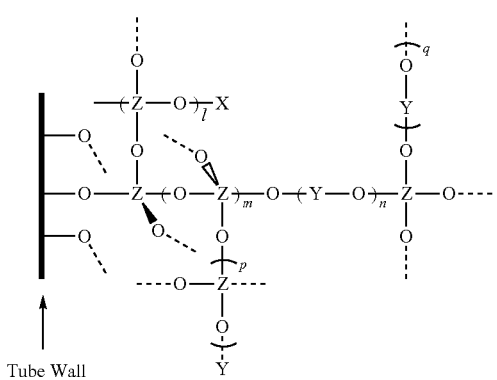

wherein,

X=Residual of a deactivation reagent (e.g., polymethylhydrosiloxane (PMHS), hexamethyldisilazane (HMDS), etc.);

Y=Sol-gel reaction residual of a sol-gel active organic molecule (e.g., molecules with hydroxysilane or alkoxysilane monomers, polydimethylsiloxane (PDMS), polymethylphenylsiloxane (PMPS), polydimethyldiphenylsiloxane (PDMDPS), polyethylene glycol (PEG) and related polymers such as Carbowax 20M, polyalkylene glycol such as Ucon, macrocyclic molecules such as cyclodextrins, crown ethers, calixarenes, alkyl moieties such as octadecyl, octyl, a residual from a baseline stabilizing agent such as bis(trimethoxysilylethyl)benzene, 1,4-bis(hydroxydimethylsilyl)benzene, etc.

Z=Sol-gel precursor-forming chemical element (e.g., Si, Al, Ti, Zr, etc.)

l=An integer ≥0;

m=An integer ≥0;

n=An integer ≥0;

p=An integer ≥0;

q=An integer ≥0; and l, m, n, p, and q are not simultaneously zero.

Dotted lines indicate the continuation of the chemical structure with X, Y, Z, or Hydrogen (H) in space.

In the preparation of gas chromatography columns, it is desirable to use sol-gel solutions to coat the walls of capillary tube structures for the separation of analytes. These sol-gels are prepared by standard methods known in the art and comprise both polysiloxane and non-polysiloxane type gels. These include, but are not limited to, polysiloxane-based gels with a wide range of substituted functional groups, including: methyl, phenyl, cyanoalkyl, cyanoaryl, etc. in addition, sol-gel polyethylene glycols such as, but not limited to, PEG, Carbowax, Superox, sol-gel alkyl, sol-gel polyalkylene oxides, such as Ucon, and other sol-gels, such as sol-gel dendrimers can be modified by the instant invention.

In order to achieve the desired sol-gels of the instant invention, certain reagents in a reagent system were preferred for the fabrication of the gels for the columns of the present invention. The reagent system included two sol-gel precursors, a sol-gel active polymer or ligand, a deactivation reagent, one or more solvents and one or more a catalysts. For the purposes of this invention, the precursors utilized for preparing the sol-gel coated GC capillary columns of the present invention have the general structure of:

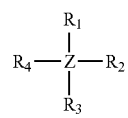

wherein,

Z is the precursor-forming element taken from a group including, but not limited to, silicon, aluminum, titanium, zirconium, vanadium, germanium, and the like; and $R_1$, $R_2$, $R_3$, and $R_4$ (i.e., "R-groups") are substituent groups at least two of which are sol-gel-active, wherein the sol-gel active groups include, but are not limited to, alkoxy, hydroxy moieties, and the like. Typical sol-gel-active alkoxy groups include, but are not limited to, a methoxy group, ethoxy group, n-Propoxy group, isoPropoxy group, n-butoxy group, isobutoxy group, tert-butoxy group, and any other alkoxy groups known to those of skill in the art. If there are any remaining R-groups, they can be any non sol-gel active groups such as methyl, octadecyl, phenyl, and the like. It is preferred however, that three or four of the R-groups are sol-gel active groups.

Typical non-sol-gel-active substituents of the precursor-forming element (Z) include, but are not limited to, alkyl moieties and their derivatives, alkenyl moieties and their derivatives, aryl moieties and their derivatives, arylene moieties and their derivatives, cyanoalkyl moieties and their derivatives, fluoroalkyl moieties and their derivatives, phenyl moieties and their derivatives, cyanophenyl moieties and their derivatives, biphenyl moiety and its derivatives, cyanobiphenyl moieties and their derivatives, dicyanobiphenyl moieties and their derivatives, cyclodextrin moieties and their derivatives, crown ether moieties and their derivatives, cryptand moieties and their derivatives, calixarene moieties and their derivatives, liquid crystal moieties and their derivatives, dendrimer moieties and their derivatives, cyclophane moieties and their derivatives, chiral moieties, polymeric moieties, and any other similar non-sol-gel active moieties known to those of skill in the art.

In addition to the above mentioned and preferred precursors, other precursors can be used with the present invention. These precursors include, but are not limited to, a chromatographically active moiety selected from the group of octadecyl, octyl, cyanopropyl, diol, biphenyl, and phenyl. Other representative precursors include, but are not limited to, Tetramethoxysilane, 3-(N-styrylmethyl-2-aminoethylamino)-propyltrimethoxysi lane hydrochloride, N-tetradecyldimethyl(3-trimethoxysilylpropyl)ammonium chloride, N-(3-trimethoxysilylpropyl)-N-methyl-N,N-diallylammonium chloride, N-trimethoxysilylpropyltri-N-butylammonium bromide, N-trimethoxysilylpropyl-N,N,N-trimethylammonium chloride, Trimethoxysilylpropylthiouronium chloride, 3-[2-N-benzyaminoethylaminopropyl]trimethoxysilane hydrochloride, 1,4-Bis(hydroxydimethylsilyl)benzene, Bis(2-hydroxyethyl)-3-aminopropyltriethoxysilane, 1,4-bis(trimethoxysilylethyl)benzene, 2-Cyanoethyltrimethoxysilane, 2-Cyanoethyltriethoxysilane, (Cyanomethylphenethyl)trimethoxysilane, (Cyanomethylphenethyl)triethoxysilane, 3-Cyanopropyldimethylmethoxysilane, 3-Cyanopropyltriethoxysilane, 3-Cyanopropyltrimethoxysilane, n-Octadecyltrimethoxysilane, n-Octadecyidimethylmethoxysilane, Methyl-n-Octadecyidiethoxysilane, Methyl-n-Octadecyldimethoxysilane, n-Octadecyltriethoxysilane, n-Dodecyltriethoxysilane, n-Dodecyltrimethoxysilane, n-Octyltriethyoxysilane, n-Octyltrimethoxysilane, n-Ocyidiisobutylmethoxysilane, n-Octylmethyidimethoxysilane, n-Hexyltriethoxysilane, n-isobutyltriethoxysilane, n-Propyltrimethoxysilane, Phenethyltrimethoxysilane, N-Phenylaminopropyltrimethoxysilane, Styrylethyltrimethoxysilane, 3-(2.2,6,6-tetramethylpiperidine-4-oxy)-propyltriethoxysiiane, N-(3-triethoxysilylpropyl)acetyl-glycinamide, (3,3,3-trifluoropropyl)trimethoxysilane, (3,3,3-trifluoropropyl)methyldimethoxysilane, 3-mercaptopropyltrimethoxysilane, 3-mercaptopropyltrimethoxysilane, 3-mercaptopropyltriethoxysilane, mercaptomethylmethyldiethoxysilane, 3-mercaptopropylmethyldimethoxysilane, 3-mercaptopropyloctadecyidimethoxysilane, 3-mercaptopropylloctyldimethoxysilane, 3-mercaptopropylcyanopropyldimethoxysilane, 3-mercaptopropyloctadecyldiethoxysilane, and any other similar precursor known to those of skill in the art.

The deactivation reagents include, but is not limited to, hydrosilanes, polymethylhydrosiloxianes, polymethylphenyl hydrosiloxanes, polymethyl cyanopropyl hydrosioloxanes, and any other similar deactivation reagent known to those of skill in the art. The primary catalyst includes, but is not limited to, trifluoroacetic acid, any acid, base, fluoride, and any other similar catalyst known to those of skill in the art.

According to the present invention, in addition to the above-mentioned materials, the performance of the sol gel stationary phase is improved by the addition of at least one baseline stabilizing reagent and at least one additional surface deactivation reagent to the sol solution. The baseline-stabilizing reagent prevents rearrangement of the sol-gel polymeric stationary phase and formation of volatile compounds at elevated temperature. In order to do so, the baseline-stabilizing reagent incorporates with the phenyl ring in the polymer backbone structure at room temperature using a sol-gel process. The baseline-stabilizing reagent includes, but is not limited to, bis(trimethoxysilylethyl)-benzene (BIS), phenyl-containing groups, cyclohexane containing groups, and any other similar sol-gel active stabilizing reagent known to those of skill in the art. In one embodiment, the baseline-stabilizing reagent is used in conjunction with methyltrimethoxysilane (a sol-gel percursor), and two sol-gel catalysts (trifluoroacetic acid and ammonium fluoride). First the sol-gel reactions are carried out for ten minutes using trifluoroacetic acid as the primary catalyst. After this, a second sol-gel catalyst is used to improve the condensation process for the sol-gel coating and its bonding with the capillary inner surface. The second sol-gel catalyst includes, but is not limited to, ammonium fluoride, base, fluoride, and any other similar catalysts known to those of skill in the art. It is known that under acidic conditions the hydrolysis reaction proceeds faster to produce primarily linear polymeric structure, but the polycondensation reaction remains slow. The addition of fluoride increases the polycondensation reaction rate.

Finally, a surface derivatization reagent is added as a secondary deactivation reagent, which includes, but is not limited to, 1,1,1,3,3,3-heaxmethyldisilazane, any hydrosilane, and any other similar surface deactivation reagents known to those of skill in the art. The sol-gel reactions involved in the formation of the polysiloxane structure described herein, incorporation of phenyl ring, and chemical bonding of the polymer to the column inner walls are illustrated in FIGS. 14-21 for sol-gel PDMS and sol-gel PEG.

The preparation of the sol-gel coating includes the steps of providing the tube structure, providing a sol-gel solution including one or more sol-gel precursors, an organic material with at least one sol-gel active functional group, one or more sol-gel catalysts, one or more deactivation reagents, and a solvent system. The sol-gel solution is then reacted with a portion of the tube (e.g., inner surface) under controlled conditions to produce a surface bonded sol-gel coating on the portion of the tube. The free portion of the solution is then removed from the tube under pressure, purged with an inert gas, and is heated under controlled conditions to cause the deactivation reagent to react with the surface bonded sol-gel coating to deactivate and to condition the sol-gel coated portion of the tube structure. Preferably, the sol-gel precursor includes an alkoxy compound. The organic material includes a monomeric or polymeric material with at least one sol-gel active functional group. The sol-gel catalyst is taken from the group consisting of an acid, a base and a fluoride compound, and the deactivation reagent includes a material reactive to polar functional groups (e.g., hydroxyl groups) bonded to the sol-gel precursor-forming element in the coating or to the tube structure.

The specific steps for fabrication starts with the cleaning and hydrothermal treatment of a fused silica capillary. Then, the preparation of the sol-gel solution utilizing the above precursors is done. Next, the inner walls of the hydrothermally treated capillary column are coated with the prepared sol-gel solution. Finally, conditioning of the sol-gel coated capillary tube is performed.

Referring now to FIG. 2, the selected capillary column 10 is filled with the prepared sol-gel solution utilizing the device 20 as illustrated in FIG. 2. The device 20 includes a metallic cylindrical pressurization chamber 22 and a bottom cap 24. The bottom cap is removably attached to a distal end thereof by a screw-threaded portion 34. It is understood that any attachment mechanism can be used to secure the bottom cap 24 to the distal portion of the chamber 22. A proximal end of the chamber 22 has a second sealing mechanism 36 with an outlet mechanism 26, generally in the form of a cross or any other suitable shape as desired, extending therefrom. This outlet mechanism 26 has outwardly extending portions 38, 40, 42 with outlet valves 28, 30 contained within the radially extending portions or arms thereof. The upwardly extending portion of the outlet means 26 has a capillary column 10 extending therefrom, which is removably inserted through the upwardly extending arm of the outlet device.

As previously mentioned, the sol-gel solution of the present invention utilizes various sol-gel precursors. In one embodiment, the sol-gel solution is prepared by mixing two solutions together that are each prepared in separate polypropylene vials. The first solution contains hydroxy-terminated polydimethylsiloxane (PDMS), hydroxy-terminated polydimethyldiphenylsiloxane (PDMDPS), polymethylhydrosiloxane (PMHS) and methylene chloride. The second solution is methyltrimethoxysilane, bis(trimethoxysilylethyl)-benzene, 1,1,1,3,3,3-hexamethyidisilazane (HMDS) and methylene chloride. These two solutions are then admixed by vortexing and separated from the ensuing precipitate by centrifugation. The supernatant is carefully pipetted out and placed in another vial for insertion into the filling and purging device. This is accomplished by unscrewing the cap 24, inserting the vial and then replacing the cap 24 to provide an airtight seal. If necessary, Teflon tape or other suitable adhesive mechanism can also be used in the sealing of the cap 24. In addition, airtight sealing mechanism 44 is in communication with the arm member extending upwardly from the cross-like member and connecting means 46 extending from the radially extending arms.

Prior to the insertion of the vial 32 into the chamber 22, the valves 28, 30 are closed and then the capillary column 10 is inserted into the chamber 22 via the outwardly extending portion of the cross-like member 26 such that it is in contact with the sol-gel solution contained in vial 32. A gas pressure is selected depending on the size of the capillary to be filled and this pressure is applied to an inert gas applied to the chamber 22 by opening the valve 28. The sol-gel is then pushed up from the vial 32 into the capillary 10, completely filling the extent thereof. When the sol-gel solution overflows from the distal end of the capillary 10, the inlet valve 28 is closed and the outlet valve 30 is then opened to release the excess pressure from the chamber 22.

The solution is allowed to reside inside the full extent of the capillary column 10 for a desired length of time, according to the thickness of coating to be formed on the inner walls 14 of the tube structure 12 of the capillary column 10, and the sol-gel reactions take place within the capillary column 10. These reactions include chemical bonding of the inner walls 14 of the tube structure 12 with the components of the sol-gel by virtue of the silanol groups in the polymeric network reacting with the silanol groups of the silica tube structure 12. This reaction forms an immobilized sol-gel surface coating integral with the inner walls 14 of the tube structure 12. The now filled capillary is then subjected to further processing.

After the reaction period for the sol-gel solution is completed, the outlet valve 30 is closed and the inlet valve 28 is opened to allow for an inert pressurized gas to be again introduced into the capillary 10. Prior to this gas introduction, the cap 24 is opened to remove the vial 32, leaving the chamber 22 without any members other than the distal end of capillary 10 extending thereto. This gas purging allows the excess sol-gel solution, which has not yet bonded to the capillary walls to be purged from the capillary 10 via its distal end. Purging with the inert gas also removes any residual solvent or other volatiles from the capillary 10.

Final conditioning of the capillary 12 is accomplished by sealing the ends of the capillary after it is removed from the device 20 by use of any known sealing means such as an oxy-acetylene torch. A programmed system of heating is then applied to the capillary and then the seals are removed to allow for solvent rinsing after which a final programmed temperature drying with simultaneous inert gas purging is performed. The column thus prepared is ready then for use.

The above discussion provides a factual basis for the use of the column and related method described herein. The methods used with a utility of the present invention can be shown by the following non-limiting examples and accompanying figures.

EXAMPLES

The following examples specifically provide for the specific methods and materials utilized with the present invention.

Materials:

Fused silica capillary (250 μm i.d.) can be obtained from Polymicro Technologies Inc. (Phoenix, Ariz., USA). HPLC-Grade tetrahydrofuran (THF), methylene chloride, and methanol were purchased from Fisher Scientific (Pittsburgh, Pa., USA). Tetramethoxysilane (TMOS, 99+%), poly(methylhydrosiloxane) (PMHS), and trifluoroacetic acid (containing 5% water), were purchased from Aldrich (Milwaukee, Wis., USA) Hydroxy-terminated poly(dimethylsiloxane) (PDMS), methyl-trimethoxysilane (MTMS) and trimethylmethoxysilane (TMMS) were purchased from United Chemical Technologies, Inc. (Bristol, Pa., USA). Ucon 75-H-90,000 polymer was obtained from Alltech (Deerfield, Ill., USA).

Gas chromatographic experiments have been carried out on a Shimadzu Model 14A capillary GC system. A Jeol Model JSM-35 scanning electron microscope has been used for the investigation of coated surfaces. A homemade capillary filling device has been used for filling the capillary with the coating sol solution using nitrogen pressure. A Microcentaur Model APO 5760 centrifuge has been used to separate the sol solution from the precipitate. A Fisher Model G-560 Vortex Genie 2 system has been used for thorough mixing of various solution ingredients. A Barnstead Model 04741 Nanopure deionized water system was used to obtain 17.8 MΩ water.

Example One

The inner surface of an appropriate length of a fused silica capillary is cleaned by sequentially rinsing with 5 ml each of the following solvents:
 (a) methylene chloride;
 (b) methanol; and
 (c) deionized water.

The capillary is then purged with a flow of helium, or any other inert gas, for 5 minutes leaving behind a thin coating of deionized water on the inner surface of the capillary. The two ends of the capillary are then sealed with an oxy-acetylene flame. The sealed capillary was then heated by programming the temperatures from an initial value of 40° C. to a final value of 300° C. at a rate of change of 4° C. per minute, and allowing the thermal treatment at the final temperature to continue for approximately 120 minutes. The capillary was allowed to cool down to room temperature, and then the ends are cut open. The capillary was then purged again with an inert gas, the flow rate being 1 ml per minute while being simultaneously heated at the same programmed temperature as delineated before.

| Two solutions were then prepared in separate polypropylene vials: | |
|---|---|
| (1) Solution 1: | |
| (a) Hydroxy-terminated Polydimethylsiloxane (PDMS) | 0.025 g |
| (b) Hydroxy-terminated Polydimethyldiphenylsiloxane (PDMDPS) | 0.025 g |
| (c) Polymethylhydrosiloxane (PMHS) | 25 μl |
| (d) Methylene chloride | 600 μl |
| (2) Solution 2: | |
| (a) Methylteimethoxysilane (MTMS) | 5 μl |
| (b) bis(trimethoxysilylethyl)-benzene | 10 μl |

-continued

Two solutions were then prepared in separate polypropylene vials:

| | |
|---|---|
| (c) 1,1,1,3,3,3-hexamethyldisilazane (HMDS) | 10 µl |
| (d) methylene chloride | 280 µl |

The solutions were then mixed together by thorough vortexing. This was followed by the addition of 50 µl of trifluoroacetic acid (containing 5% water) and vortexed again. Further, a 20 µl volume of a methanolic solution of ammonium fluoride (20 mg/ml) was added to the mixture. The precipitate was separated out by centrifugation and the supernatant was carefully pipetted out and transferred to a clean vial. This final sol-gel solution was then further used to coat the capillary column.

The pre-treated capillary tube was then filled with the sol-gel solution and allowed to sit for a selected residence time (e.g. 10-30 minutes). This allowed the sol-gel polymer to be formed in the sol solution and get bonded to the inner walls of the capillary. The excess, unreacted sol-gel solution was then expelled from the capillary under helium or other inert gas pressure, leaving the surface-bonded coating on the inner surface of the capillary tube. Volatiles and residual solvents or sol-gel solution were then purged off the tube using helium or other inert gas for 30-60 minutes.

Both ends of the now coated and gas-filled capillary were sealed and then heated by use of a programmed temperature sequence. This sequence was as follows, but other modifications of this are within the scope of the present invention:
(1) Heating from 40° C. to 150° C. at 1° C. per minute with an incremental change with a hold time of 5 hours at 150° C.
(2) Heating the column from 150° C. at programmed sequential increments to a final temperature of 350° C. or any other temperature suitable for the selected sol-gel matrix. This heating was allowed to continue for a hold time of approximately 60 minutes.
(3) Opening of the ends of the column.
(4) Rinsing of the column with a selected solvent mixture, e.g. 1:1 v/v methylene chloride/methanol mixture.
(5) Drying of the coated capillary under helium purge and further temperature programming conditions; e.g., 40° C. to 350° C. at 6° C. per minute.

The column was then ready for use in chromatographic analysis. In order to test the efficacy of the columns of the present invention, several columns were prepared with and without the preferred reagents of the present invention.

Example Two

Preparation of Columns with and without Ammonium Fluoride

| Solution 1 (for column without ammonium fluoride): | |
|---|---|
| PDMS | 0.025 g |
| Polydimethyldiphenylsiloxane in 200 µl methyl chloride | 0.025 g |
| PMHS | 25 µl |
| Methyl chloride | 400 µl |
| Solution 2 (for column without ammonium fluoride): | |
| M-TMOS | 5 µl |
| BIS | 10 µl |
| HMDS | 10 µl |
| Methylene chloride | 310 µl |

As before, the two solutions were combined and introduced into a fused silica capillary tube and post-treated according to the method above. A GROB test mixture was then run.

| Solution 3 (for column with ammonium fluoride): | |
|---|---|
| PDMS | 0.025 g |
| Polydimethyldiphenylsiloxane in 200 µl methylene chloride | 0.025 g |
| PMHS | 25 µl |
| Methylene chloride | 400 µl |
| Solution 4 (for column with ammonium fluoride): | |
| M-TMOS | 5 µl |
| BIS | 10 µl. |
| HMDS | 10 µl |
| Methylene chloride | 310 µl |

Again, solutions 3 and 4 were mixed together, however, in addition 50 µl TFA (5% water), 20 µl of methanolic ammonium fluoride were added after the initial mixing and centrifuging. Another test solution was run on this column after the final treatment steps.

Figure 3A:
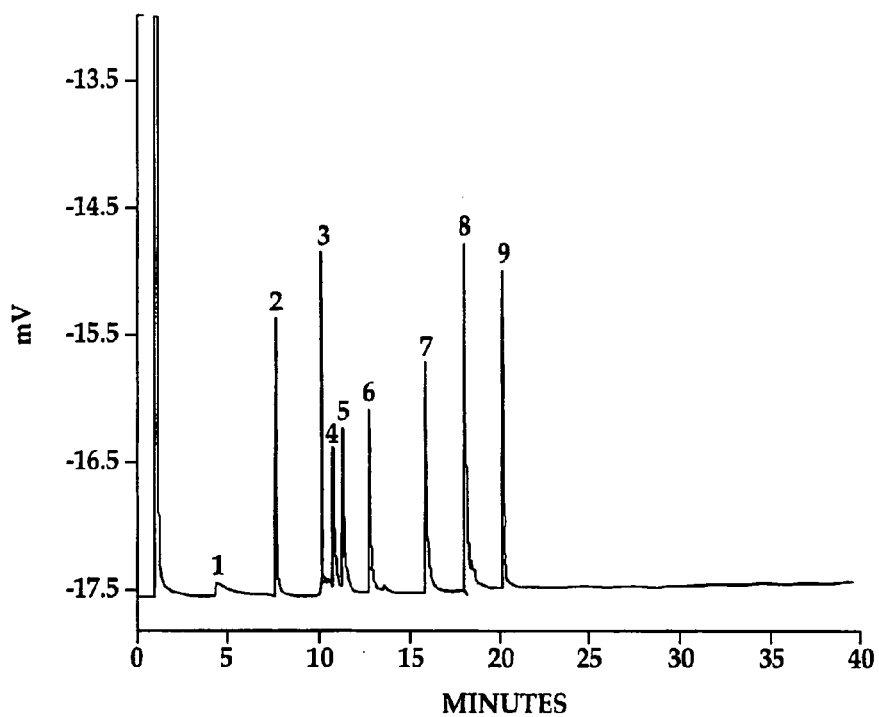
FIG. 3A. GC separation of Grob test mixture on a sol-gel-coated PDMS column prepared using a sol solution containing hydroxy-terminated polydimethylsiloxane, poly dimethyl (82-86%) diphenyl (14-18%) siloxane, hydroxy-terminated poly(methylhydrosiloxane), methyltrimethoxysilane, 1,1,1,3,3,3,-hexamethyldisilazane, trifluoroacetic acid, and bis(trimethoxysilylethyl)benzene, but no ammonium fluoride, wherein the conditions are: 10-m×250-μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$ with peaks (1) 2,3-butanediol, (2) n-decane, (3) 1-octanol, (4) 1-nonanal (5) n-undecane, (6) 2,6-dimethylaniline, (7) methyl decanoate, (8) methyl undecanoate, and (9) methyl dodecanoate.
Figure 3B:
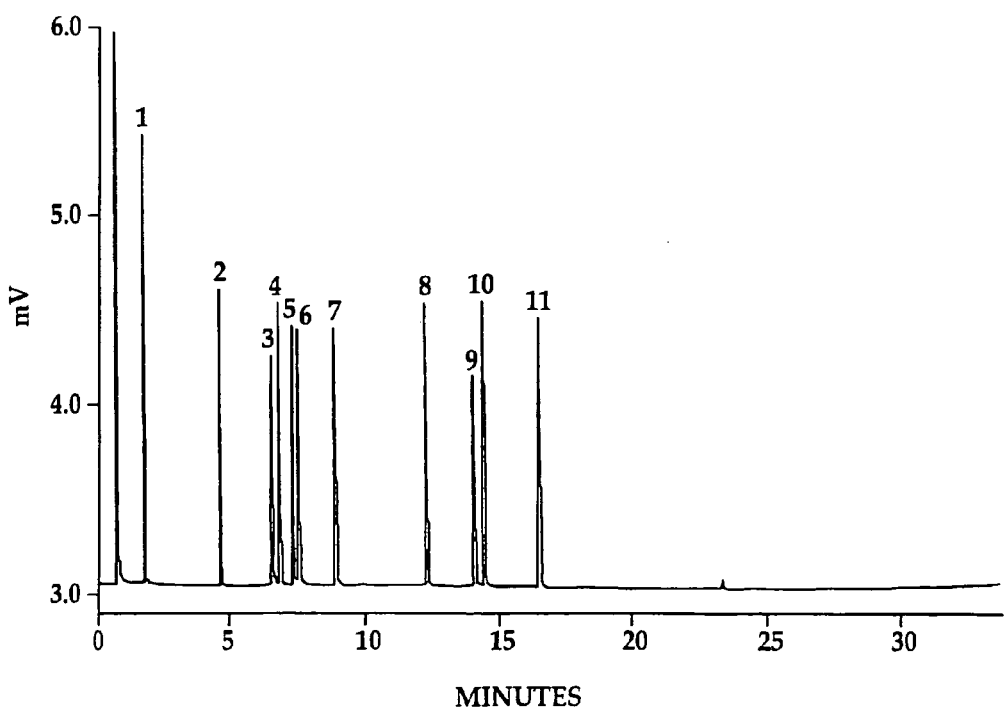
FIG. 3B. GC separation of Grob test mixture on a sol-gel-coated PDMS capillary column prepared using a sol solution containing hydroxy-terminated polydimethylsiloxane, hydroxy-terminated poly dimethyl (82-86%) diphenyl (14-18%) siloxane, poly(methylhydrosiloxane), methyltrimethoxysilane, 1,1,1,3,3,3-hexamethyldisilazane, trifluoroacetic acid, and both ammonium fluoride and bis(trimethoxysilylethyl)benzene, wherein the conditions are: 10-m×250 μm-i.d. fused silica capillary column; stationary phase, sol-gel PDMS; carrier gas, helium; injection, split (100:1, 300° C.); detector, FID, 350° C.; temperature programming from 40° C. at 6° C. minutes$^{-1}$ with peaks (1) 2,3-butanediol, (2) n-decane, (3) 1-octanol, (4) 2,6-dimethylphenol, (5) 1-nonanal, (6) n-undecane, (7) 2,6-dimethylaniline (8) methyl decanoate, (9) dicyclohexylamine, (10) methyl undecanoate and (11) methyl dodecanoate.

Results of comparison studies of columns prepared without and with the ammonium fluoride are illustrated in FIGS. 3 A and 3 B.

Example Three

Preparation of Columns with and without BIS

| Solution 1 (with BIS): | |
|---|---|
| PDMS | 0.025 g |
| Polydimethyldiphenylsiloxane with 200 µl methylene chloride | 0.025 g |
| PMHS | 25 µl |
| Methylene chloride | 400 µl |
| Solution 2 (with BIS): | |
| M-TMOS | 5 µl |
| BIS | 10 µl |
| HMDS | 5 µl |
| Methylene chloride | 285 µl |

The vials were admixed as above and after centrifuging for 10 minutes, the ammonium fluoride catalyst is added to the mixture. The column was prepared by the method presented before.

| Solution 3 (without BIS): | |
|---|---|
| PDMS | 0.025 g |
| Polydimethyldiphenylsiloxane in 200 µl methylene chloride | 0.025 g |
| PMHS | 25 µl |
| Methylene chloride | 400 µl |
| Solution 4 (without BIS): | |
| M-TMOS | 5 µl |
| HMDS | 5 µl |
| Methylene chloride | 285 µl |

As above, the columns was prepared according to the procedure outlined before.

Both columns were tested using a GROB test mixture and the resulting spectra are shown in FIGS. 4 A and 4 B. The column with the BIS component clearly shows improved baseline stability and better peak resolution.

Example Four

| Columns Prepared With and Without HMDS | |
|---|---|
| Solution 1 (with HMDS): | |
| PDMS | 0.025 g |
| Polydimethyldiphenylsiloxane in 200 μl methylene chloride | 0.025 g |
| PMHS | 25 μl |
| Methylene chloride | 400 μl |
| Solution 2 (with HMDS): | |
| M-TMOS | 5 μl |
| BIS | 10 μl |
| HMDS | 5 μl |
| Methylene chloride | 285 μl |
| Solution 3 (without HMDS): | |
| PDMS | 0.025 g |
| Polydimethyldiphenylsiloxane in 200 μl of methylene chloride | 0.025 g |
| PMHS | 25 μl |
| Methylene chloride | 400 μl |
| Solution 4 (without HMDS): | |
| M-TMOS | 5 μl |
| BIS | 10 μl |
| Methylene chloride | 290 μl |

The columns were again prepared by the methods already disclosed, including the addition of the ammonium fluoride catalyst step. The results of the spectra of GROB test solution runs are shown in FIGS. 5 A and 5 B. Again, the addition of the HMDS gave improved results.

Example Five

| Optimized Solution | |
|---|---|
| Solution 1: | |
| PDMS | 0.025 g |
| Polydimethyldiphenylsiloxane in 300 μl methylene chloride | 0.025 g |
| PMHS | 25 μl |
| Methylene chloride | 300 μl |
| Solution 2: | |
| M-TMOS | 5 μl |
| BIS | 10 μl |
| HMDS | 10 μl |
| Methylene chloride | 280 μl |

The columns were prepared according to the already disclosed method.

As can be seen from the above examples and Table 1, the columns of the instant invention demonstrated a reproducibility in results both run-to-run and column-to-column.

Throughout this application, various publications, including United States patents, are referenced by author and year and by patent number. Full citations for the publications are listed below. The disclosures of these publications and patents in their entireties are hereby incorporated by reference into this application in order to describe more fully the state of the art to which this invention pertains.

The invention has been described in an illustrative manner, and it is to be understood that the terminology used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE 1

Retention Time and Retention Factor Reproducibility Data Obtained on three Sol-Gel Coated PEG colum in 5 Replicate Runs

| Peak # | NAME | tr | SD | RSD % | k | SD | RSD % |
|---|---|---|---|---|---|---|---|
| COLUMN NUMBER 1 | | | | | | | |
| 1 | n-Hexadecane | 2.38 | 0.02 | 0.71 | 3.4 | 0.03 | 0.94 |
| 2 | Methyl Undecanoate | 4.48 | 0.09 | 1.96 | 7.37 | 0.10 | 1.34 |
| 3 | 1-Decanol | 2.79 | 0.00 | 0.14 | 3.72 | 0.01 | 0.24 |
| 4 | n-Octadecane | 3.63 | 0.05 | 1.38 | 5.72 | 0.09 | 1.63 |
| 5 | 2,6-Dimethylphenol | 3.15 | 0.02 | 0.67 | 4.8 | 0.04 | 0.92 |
| 6 | 2-Ethylhexanoic acid | 6.1 | 0.14 | 2.21 | 10.3 | 0.25 | 2.42 |
| 7 | Hexanophenone | 10.12 | 0.13 | 1.30 | 17.75 | 0.24 | 1.37 |
| 8 | Eicosane | 18.43 | 0.41 | 2.25 | 33.13 | 0.76 | 2.29 |
| COLUMN NUMBER 2 | | | | | | | |
| 1 | n-Hexadecane | 1.93 | 0.01 | 0.31 | 2.26 | 0.01 | 0.40 |
| 2 | Methyl Undecanoate | 2.49 | 0.00 | 0.16 | 3.22 | 0.00 | 0.12 |
| 3 | Dicyclohexylamine | 2.64 | 0.03 | 1.14 | 3.48 | 0.06 | 1.72 |
| 4 | 1-Decanol | 2.79 | 0.00 | 0.14 | 3.72 | 0.01 | 0.24 |
| 5 | n-Octadecane | 3.81 | 0.00 | 0.10 | 5.45 | 0.01 | 0.15 |
| 6 | 2,6-Dimethylphenol | 4.22 | 0.00 | 0.09 | 6.15 | 0.00 | 0.07 |
| 7 | 2-Ethylhexanoic acid | 4.87 | 0.00 | 0.08 | 7.25 | 0.01 | 0.11 |
| 8 | Hexanophenone | 6.94 | 0.01 | 0.12 | 10.70 | 0.00 | 0.00 |
| 9 | Eicosane | 8.23 | 0.01 | 0.12 | 12.92 | 0.02 | 0.15 |
| COLUMN NUMBER 3 | | | | | | | |
| 1 | n-Hexadecane | 1.50 | 0.01 | 0.80 | 1.55 | 0.02 | 1.35 |
| 2 | Methyl Undecanoate | 1.72 | 0.01 | 0.70 | 1.92 | 0.02 | 1.09 |
| 3 | Dicyclohexylamine | 1.78 | 0.01 | 0.56 | 2.01 | 0.02 | 0.75 |
| 4 | 1-Decanol | 2.29 | 0.06 | 2.53 | 2.89 | 0.10 | 3.49 |
| 5 | n-Octadecane | 2.56 | 0.00 | 0.00 | 3.33 | 0.00 | 0.00 |
| 6 | 2,6-Dimethylphenol | 2.86 | 0.01 | 0.42 | 3.84 | 0.02 | 0.52 |
| 7 | 2-Ethylhexanoic acid | 3.84 | 0.02 | 0.44 | 5.50 | 0.03 | 0.51 |
| 8 | Hexanophenone | 4.53 | 0.02 | 0.33 | 6.67 | 0.03 | 0.39 |
| 9 | Eicosane | 6.01 | 0.05 | 0.83 | 9.18 | 0.09 | 0.94 |

GC separation of polarity test mixture(TC WAX) on three sol-gel coated PEG columns prepared in the same way, using sol solutions containing different amounts of sol-gel ingredients; column, 10-m × 0.25 mm-i.d. fused silica capillary column; stationary phase, Polyethylene glycol PEG: carrier gas, helium; injection, split (100:1, 300° C.); detector, FID, 350° C.; temperature, 150° C.

REFERENCES

Abe, I.; Kameyama, K.; Wasa, T.; *Chromatographia* 27, 631-633 (1989).
Altgelt, K. H.; Gouw, T. H., *Chromatography in Petroleum Analysis*, Marcel Dekker, New York, 1979.
Bartle, K. D.; Woolley, C. L.; Markides, K. E.; Lee, M. L.; Hansen, R. S. *J. High Resolut Chromatogr./Chromatogr. Commun* 1987, 10, 128-136.
Berezkin, V. G., Drugov, I. S., *Gas Chromatography in Air Pollution Analysis*, Elsevier, Amsterdam, 1991.
Blomberg L. G., *J. Microcol, September* 1990, 2, 62-67.
Blomberg, L.; Markides, K. E.; Wannman, T. *J. High Resolut. Chromatogr. Chromatogr. Commun.* 1980, 3, 527.
Blomberg, L.; Wannman, T. *J. Chromatogr.* 1978, 148, 379-387.
Bouche, J.; Verzele, M. *J. Gas Chromatogr.* 1968, 6, 501-505.

Brinker, C. J., Scherer, G. W., *Sol-gel Science*, Academic Press, San Diego, 1990.
Clement, R. E. (ed.), *Gas chromatography: Biochemical, Biomedical, and Clinical Applications*, Wiley, New York, 1990.
de Nijs; R. C. M.; Franken, J. J.; Dooper, R. P. M.; Rijks, J. A.; de Ruwe, H. J. J. M.; Schulting, F. L. *J. Chromatogr.* 1978, 167, 231-242.
Ettre, L. S., Hinshaw, J. V. *Basic Relationship in Gas Chromatography*, Advanstar, Cleveland, USA, 1994, p. 144.
Golay, M. J. E., in Coates, V. J.; Noebels, H. J.; Faberson I. S. (eds.), *Gas Chromatography* (1957 *Lansing Symposium*), Academic Press, New York, 1958, pp. 1-013.
Lawrocki, *J. Chromatographia* 1991, 31, 177-205.
Lee, M. L.; Kong, R. C.; Woolley, C. L.; Bradshaw, J. S. *J. Chromatogr. Sci.* 1984, 22, 136-142.
Mayer, B. X. et al., *J. Chromatogr. A.*, 917, 219-226
Poole, C. F.; Poole S. K., in E. Heftman (ed.) *Chromatography, 5th Edition, Part A: Fundamentals and Techniques (J. Chromatogr. Libr.* Vol. 51A, Amsterdam, 1992), ch. 9.
Schomburg, G.; Husmann, H.; Borwitsky, H., *Chromatographia* 1979, 12, 651-660.
Sumpter, S. R.; Woolley, C. L.; Huang, E. C.; Markides, K. E.; Lee, M. L. *J. Chromatogr.* 1990, 517, 503-519.
Tebbett, I. (Ed.), *Gas Chromatography in Forensic Science*, E. Horwood, New York, 1991.
Woolley, C. L.; Kong, R. C.; Richter, B. E.; Leo, M. L., *J. High Resolut. Chromatogr. Chromatogr. Commun.* 1984, 7, 329-332.
Wright, B. W.; Peaden, P. A.; Lee M. L.; and Stark T. J., *J. Chromatogr.* 1982, 248, 17-34.
Yakabe, Y.; Sudoh, Y.; Takahata, Y. *J. Chromatogr.* 1991, 558, 323-327.

What is claimed is:

1. A gas chromatography capillary column comprising:
a tube structure including inner walls; and
a sol-gel substrate coated on a portion of said inner walls of said tube structure to form a stationary phase coating on said inner walls, said sol-gel substrate including a polymer backbone, at least one baseline stabilizing reagent residual, and at least one surface deactivation reagent residual, wherein said at least one baseline stabilizing reagent residual comprises a rigid moiety and said baseline stabilizing reagent residual is incorporated into said polymer backbone, wherein said rigid moiety is directly attached to said polymer backbone and thereby reduces flexibility of said polymer backbone and inhibits rearrangement and breakdown of said stationary phase, wherein said at least one baseline stabilizing reagent residual is bis(trimethoxysilylethyl)-benzene.

2. The capillary column according to claim 1, wherein said at least one surface deactivation reagent residual is selected from the group consisting of 1,1,1,3,3,3-hexamethyldisilazane, hydrosiloxane, and hydrosilane.

3. The capillary column according to claim 1, wherein said sol-gel substrate is made from sol-gel precursors having the general structure:

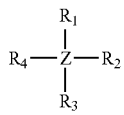

wherein,
Z=a precursor-forming element selected from the group consisting of silicon, aluminum, titanium, zirconium, vanadium, and germanium, alkyl moieties and their derivatives, alkenyl moieties and their derivatives, aryl moieties and their derivatives, arylene moieties and their derivatives, cyanoalkyl moieties and their derivatives, fluoroalkyl moieties and their derivatives, phenyl moieties and their derivatives, cyanophenyl moieties and their derivatives, biphenyl moiety and its derivatives, cyanobiphenyl moieties and their derivatives, dicyanobiphenyl moieties and their derivatives, cyclodextrin moieties and their derivatives, crown ether moieties and their derivatives, cryptand moieties and their derivatives, calixarene moieties and their derivatives, liquid crystal moieties and their derivatives, dendrimer moieties and their derivatives, cyclophane moieties and their derivatives, chiral moieties, and polymeric moieties; and
$R_1$, $R_2$, $R_3$, and $R_4$=R-groups that are moieties selected from the group consisting of sol-gel-active moieties, alkoxy moieties, hydroxy moieties, non-sol-gel-active moieties, methyl, octadecyl, and phenyl.

4. The capillary column according to claim 1, wherein said alkoxy groups are selected from the group consisting of a methoxy group, ethoxy group, n-Propoxy group, iso-Propoxy group, n-butoxy group, iso-butoxy group, and tert-butoxy group.

5. The capillary column according to claim 1, wherein at least two of said R-groups comprise moieties selected from the group consisting of sol-gel active moieties, alkoxy moieties, and hydroxy moieties.

6. The capillary column according to claim 5, wherein said R-groups other than said at least two R-groups comprise moieties selected from the group consisting of methyl, octadecyl, phenyl, and hydrogen.

7. The capillary column according to claim 1, wherein said sol-gel substrate further includes a residual deactivation reagent selected from the group consisting of polymethylhydrosiloxane and hexamethyldisilazane.

8. The capillary column according to claim 1, wherein said tube structure is made of a material selected from the group consisting of glass, fused silica, alumina, titania, and zirconia.

9. The capillary column according to claim 3, wherein said alkoxy groups are selected from the group consisting of a methoxy group, ethoxy group, n-Propoxy group, iso-Propoxy group, n-butoxy group, iso-butoxy group, and tert-butoxy group, and wherein at least two of said R-groups comprise moieties selected from the group consisting of sol-gel active moieties, alkoxy moieties, and hydroxy moieties.

* * * * *

UNITED STATES PATENT AND TRADEMARK OFFICE
CERTIFICATE OF CORRECTION

PATENT NO. : 8,685,240 B2
APPLICATION NO. : 11/599497
DATED : April 1, 2014
INVENTOR(S) : Abdul Malik et al.

It is certified that error appears in the above-identified patent and that said Letters Patent is hereby corrected as shown below:

In the Specification

Column 5,
Line 57, "hexamethyidisilazane" should read --hexamethyldisilazane--

Column 6,
Line 57, "(3) o-otoulaldehyde" should read --(3) o-toulaldehyde--

Column 10,
Line 39, "isoPropoxy" should read --iso-Propoxy--
Line 40, "isobutoxy" should read --iso-butoxy--

Column 11,
Line 3, "propyltrimethoxysi lane" should read --propyltrimethoxysilane--
Line 17, "n-Octadecyidimethylmethoxysilane"
            should read
    --n-Octadecyldimethylmethoxysilane--
Line 18, "n-Octadecyidiethoxysilane" should read --n-Octadecyldiethoxysilane--
Lines 22-23, "n-Octylmethyidimethoxysilane" should read --n-Octylmethyldimethoxysilane--
Line 34, "mercaptopropyloctadecyidimethoxysilane"
            should read
    --mercaptopropyloctadecyldimethoxysilane--

Column 13,
Line 5, "hexamethyidisilazane" should read --hexamethyldisilazane--

Signed and Sealed this
Ninth Day of September, 2014

Michelle K. Lee
*Deputy Director of the United States Patent and Trademark Office*